(12) United States Patent
Yamakawa et al.

(10) Patent No.: US 6,833,426 B2
(45) Date of Patent: Dec. 21, 2004

(54) HALOGENATED AROMATIC COMPOUND, (CO)POLYMER THEREOF, AND PROTON-CONDUCTIVE MEMBRANE COMPRISING SAME

(75) Inventors: Yoshitaka Yamakawa, Ibaraki (JP); Masayuki Takahashi, Ibaraki (JP); Kohei Goto, Ibaraki (JP)

(73) Assignee: JSR Corporation, Tokyo (JP)

( * ) Notice: Subject to any disclaimer, the term of this patent is extended or adjusted under 35 U.S.C. 154(b) by 0 days.

(21) Appl. No.: 10/347,336

(22) Filed: Jan. 21, 2003

(65) Prior Publication Data

US 2003/0173547 A1 Sep. 18, 2003

(30) Foreign Application Priority Data

Jan. 22, 2002 (JP) ........................................ 2002-013450

(51) Int. Cl.[7] ........................ C08G 65/00; C08G 67/00
(52) U.S. Cl. ........................ 528/86; 528/125; 528/127; 528/391; 528/397
(58) Field of Search ........................ 528/86, 125, 127, 528/391, 397

(56) References Cited

U.S. PATENT DOCUMENTS 5,071,448 A   12/1991   Bikson et al.

FOREIGN PATENT DOCUMENTS

| EP | 1 138 712   | 10/2001 |
|----|-------------|---------|
| EP | 1 245 554   | 10/2002 |
| EP | 1 245 555   | 10/2002 |
| WO | WO 00/51716 | 9/2000  |

*Primary Examiner*—Duc Truong
(74) *Attorney, Agent, or Firm*—Oblon, Spivak, McClelland, Maier & Neustadt, P.C.

(57) ABSTRACT

A halogenated aromatic compound, a polyarylene (co)polymer obtained by the polymerization of such a halogenated aromatic compound as a monomer component, and a proton-conductive membrane made of a sulfonation product of such a (co)polymer are disclosed. The halogenated aromatic compound is represented by the following general formula (1bm):

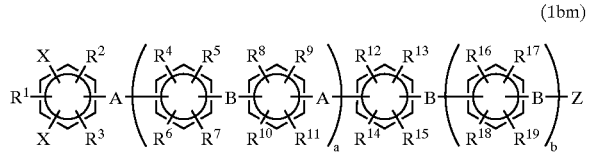

(1bm)

wherein As' independently represent an electron-withdrawing group; Bs' independently represent an electron-donating atom or divalent group; Xs' independently represent a chlorine atom, an iodine atom, or a bromine atom; Z represents an aryl group; $R^1$ to $R^{19}$ may be the same or different and each represents a hydrogen atom, a fluorine atom, an alkyl group, or a fluoroalkyl group; and a and b each represents an integer of 1 to 20.

10 Claims, 6 Drawing Sheets

HALOGENATED AROMATIC COMPOUND, (CO)POLYMER THEREOF, AND PROTON-CONDUCTIVE MEMBRANE COMPRISING SAME

FIELD OF THE INVENTION

The present invention relates to a novel halogenated aromatic compound, a polyarylene (co)polymer obtained by the polymerization of such a halogenated aromatic compound as a monomer component, and a proton-conductive membrane comprising a sulfonation product of such a (co)polymer. It is known that a proton-conductive membrane can be used as a proton-conductive membrane for primary battery electrolyte, secondary batter electrolyte, fuel cell polymer solid electrolyte, display element, various sensors, signal medium, solid capacitor, ion exchange membrane, etc.

DESCRIPTION OF THE RELATED ART

Electrolytes are usually used as (aqueous) solutions in many cases. In recent years, however, there is a growing tendency to replace such aqueous electrolytes with solid electrolytes. The first reason for this is the easiness of processing in applications of solid electrolytes, e.g., the electrical/electronic materials mentioned above. The second reason is the trend toward reduction in weight, thickness, length and size, and toward energy saving.

Conventional proton-conductive materials include both inorganic materials and organic materials. Examples of the inorganic materials include uranyl phosphates which form hydrates. However, these inorganic compounds are insufficient in interfacial contact to pose many problems concerning the formation of a conductive layer on a substrate or electrode.

On the other hand, examples of the organic compounds include organic polymers such as polymers belonging to the so-called cation-exchange resins, e.g., sulfonated vinyl polymers such as sulfonated polymers with a perfluoroalkylsulfonic acid represented by Nafion (manufactured by E. I. Du Pont de Nemours & Co., Inc.), and perfluoroalkylcarboxylic acid polymers, and polymers prepared by incorporating sulfonic acid groups or phosphoric acid groups into heat-resistant polymers such as polybenzimidazole and poly (ether ether ketone)s [see *Polymer Preprints, Japan*, Vol. 42, No. 7, pp. 2490–2492 (1993); *Polymer Preprints, Japan*, Vol. 43, No. 3, pp. 735–736 (1994); and *Polymer Preprints, Japan*, Vol. 42, No. 3, p. 730 (1993)].

These organic polymers are usually used in the form of a film. A conductive membrane made of such an organic polymer can be bonded to an electrode while taking advantage of the solvent solubility or thermoplasticity. However, many of these organic polymers have the following problems besides being still insufficient in proton conductivity. The organic polymers deteriorate in durability or in proton conductivity at elevated temperatures (100° C. or higher). When sulfonated, the organic polymers undergo embrittlement, deteriorate in mechanical strength and have a great dependence on humidity conditions. Further, the adhesion of the organic polymers to the electrode is not fully satisfactory. Moreover, the conductive membrane swells excessively during operation due to the hydrophilic polymer structure, and this swelling leads to a decrease in strength properties or a deformation. Consequently, application of those organic polymers to the aforementioned electrical/electronic materials and the like pose various problems.

U.S. Pat. No. 5,403,675 proposes a solid polymer electrolyte comprising a sulfonated rigid polyarylene. This polymer is produced from a polymer comprising a phenylene chain obtained by polymerizing an aromatic compound (the polymer structure is described at column 9 in the patent specification) by reacting the phenylene polymer as the main component with a sulfonating agent to incorporate sulfonic acid groups thereinto. However, the incorporation of a large amount of sulfonic acid groups results in a sulfonated polymer having considerable deterioration in mechanical properties such as toughness (e.g., elongation at break, flexing resistance) and hot water resistance although proton conductivity improves with the increasing amount of sulfonic acid groups incorporated.

SUMMARY OF THE INVENTION

Accordingly, one object of the invention is to provide a (co)polymer that is superior in mechanical properties such as oxidation resistance, hot water resistance, heat resistance, and toughness and that even when sulfonated, the association efficiency is high so that even when the incorporation amount of sulfonic acid groups is relatively low, not only it has efficient proton conductivity, but also it hardly deteriorates in the aforementioned properties.

Another object of the invention is to provide a sulfonic acid group-containing (co)polymer obtained by sulfonating the (co)polymer.

Still another object of the invention is to provide a proton-conductive membrane comprising the sulfonic acid group-containing (co)polymer that is superior in the aforementioned properties and has efficient proton conductivity.

These objects of the invention will become apparent from the following detailed description and examples.

First, the invention is to provide a compound useful as a monomer effective for the incorporation of sulfonic acid groups in a (co)polymer. The compound is a halogenated aromatic compound represented by the following general formula (1bm):

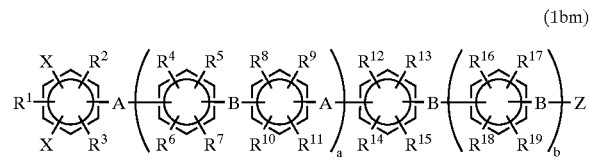

(1bm)

wherein As' independently represent an electron-withdrawing group; Bs' independently represent an electron-donating atom or divalent group; Xs' independently represent a chlorine atom, an iodine atom, or a bromine atom; Z represents an aryl group; $R^1$ to $R^{19}$ may be the same or different and each represents a hydrogen atom, a fluorine atom, an alkyl group, or a fluoroalkyl group; and a and b each represents an integer of 1 to 20.

The halogenated aromatic compound provides a (co) polymer with a structure that is readily sulfonated to enhance the effective sulfonation of the (co)polymer.

Second, the invention is to provide a polyarylene (co) polymer having a repeating unit represented by the following general formula (1b):

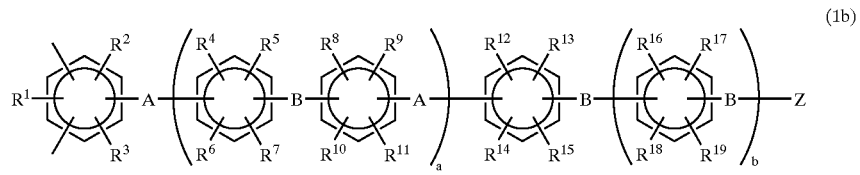

(1b)

wherein A, B, Z, $R^1$ to $R^{19}$, and a and b are the same as defined above.

The polyarylene (co)polymer may be a homopolymer or a copolymer containing other repeating units.

Third, the invention is to provide a polyarylene copolymer having a repeating unit represented by the general formula (1b) and a repeating unit comprising other divalent aromatic group.

Fourth, the invention is to provide as one of the foregoing copolymers a polyarylene copolymer wherein the repeating unit comprising other divalent aromatic group is a unit presented by the following general formula (1a):

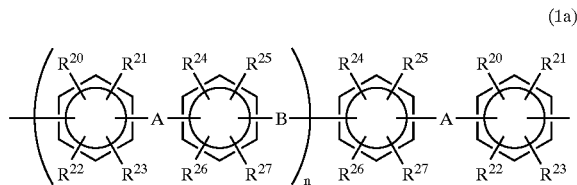

(1a)

wherein As' independently represent an electron-withdrawing group; Bs' independently represent an electron-donating atom or divalent group; $R^{20}$ to $R^{27}$ may be the same or different and each represents a hydrogen atom, a fluorine atom, an alkyl group, or a fluoroalkyl group; and n represents 0 or an integer of 1 to 20.

Since the copolymer has a flexible structure, its toughness is enhanced.

Fifth, the invention is to provide the foregoing (co) polymer further containing a sulfonic acid group.

The sulfonic acid group-containing (co)polymer is useful as a material of proton-conductive membrane.

Sixth, the invention is to provide a proton-conductive membrane comprising the foregoing sulfonic acid group-containing (co)polymer.

DETAILED DESCRIPTION OF THE INVENTION

Figure 1:
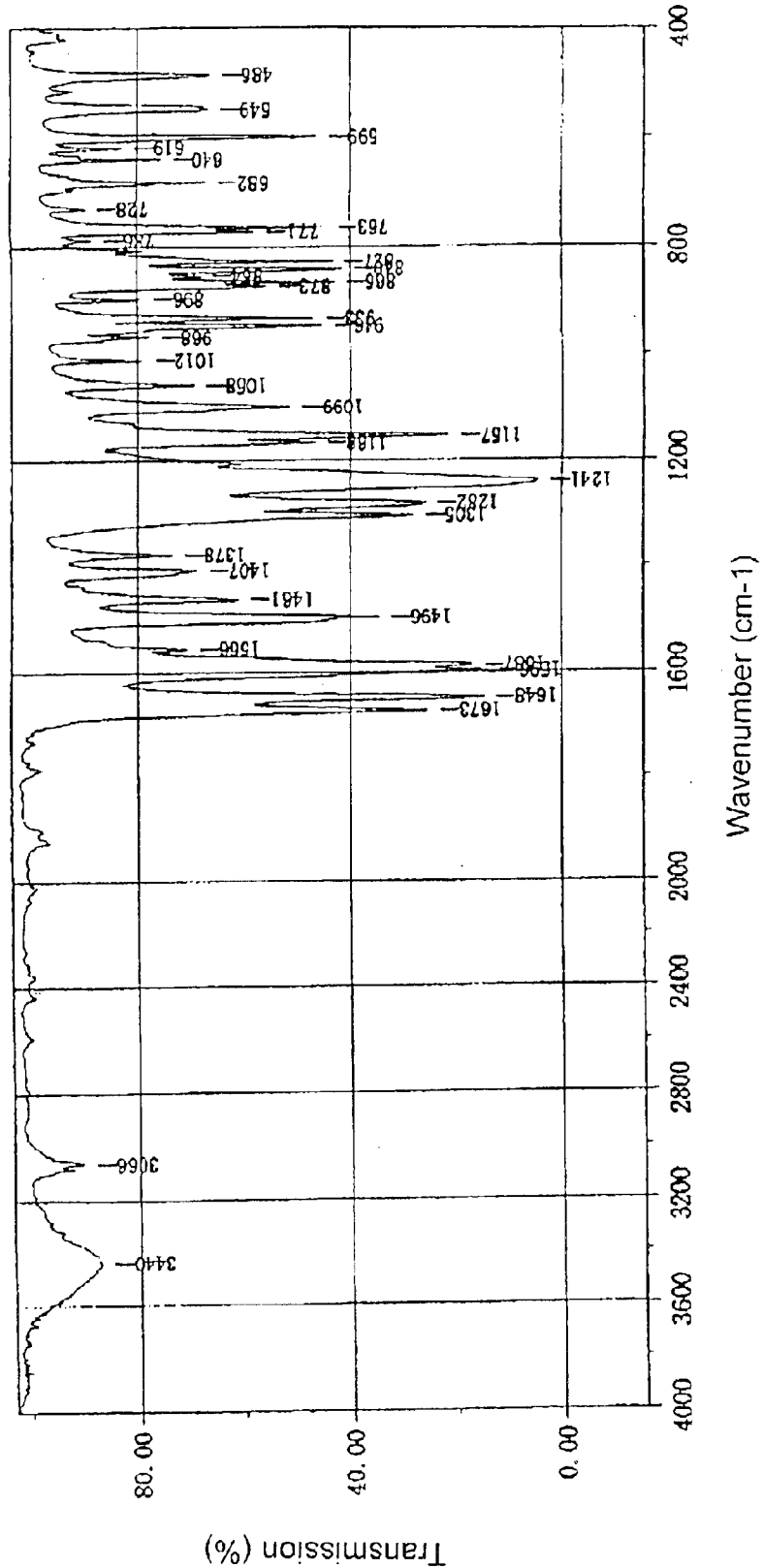
FIG. 1 is an IR spectrum of 2,5-dichloro-4'-[4-(4-fluorobenzoyl)phenoxy] benzo-phenone obtained in Example 1-(2).

The invention will be described below in detail.

Halogenated Aromatic Compound

The halogenated aromatic compound represented by the general formula (1bm) (hereinafter referred to as "monomer (B)") forms a long-side chain structure in a (co)polymer containing it as a monomer unit. When the (co)polymer is sulfonated, the proton association efficiency of the bonded sulfonic acid group is enhanced. As a result, it is possible to realize a proton conductivity of conventionally known sulfonated (co)polymers at a relatively low sulfonic acid group equivalent. Consequently, it is possible to inhibit a reduction of physical properties (such as hot water resistance, toughness, and oxidation resistance) by the sulfonation and improve such a reduction.

The general formula (1bm) will be described hereinafter.

Examples of X include a chlorine atom, a bromine atom, and an iodine atom.

A is an electron-withdrawing group such as >CO, —CONH—, —(CF$_2$)$_p$— (wherein p represents an integer of from 1 to 10), —C(CF$_3$)$_2$—, —COO—, —SO—, and —SO$_2$—. The term "electron-withdrawing group" as used herein is meant to indicate a group having a Hammett's substituent constant of 0.06 or more in the case of the m-position of the phenyl group and of 0.01 or more in the case of the p-position of the phenyl group, respectively.

B is an electron-donating group or atom such as —O—, —S—, —CH=CH—, —C≡C—,

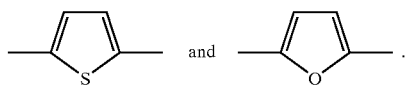

Examples of the alkyl group include a methyl group and an ethyl group; and examples of the fluoroalkyl group include a trifluoromethyl group and a pentafluoroethyl group.

a and b each represents an integer of 1 to 20, preferably 1 to 10, and more preferably 1 to 5.

Examples of the monomer (B) of the invention include compounds represented by the following chemical formulae.

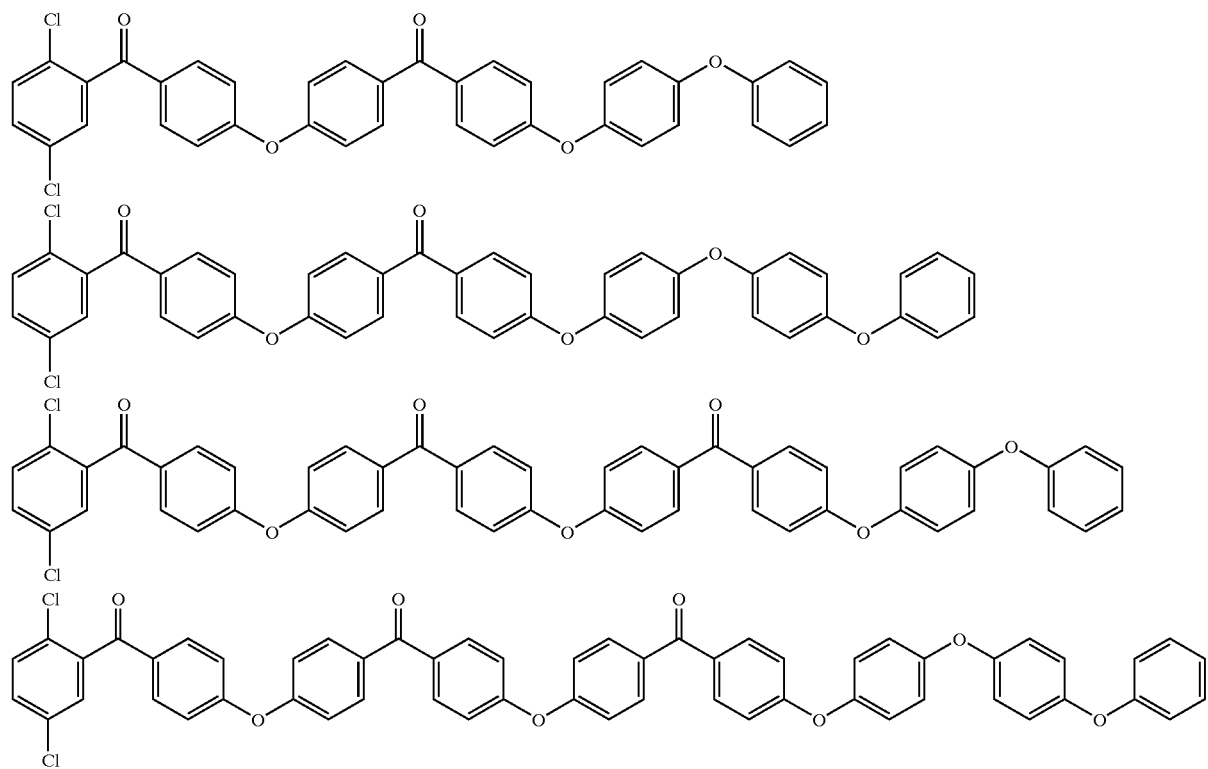
Other examples are compounds represented by the following chemical formulae.
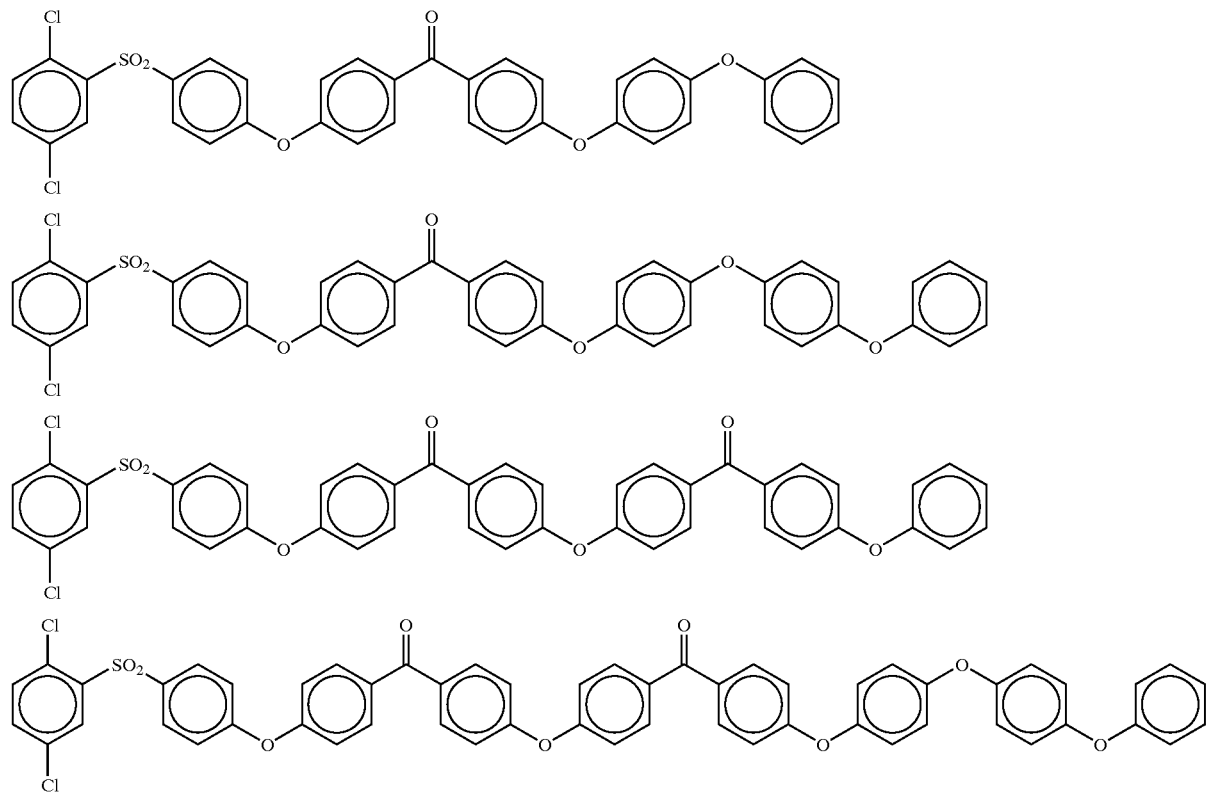

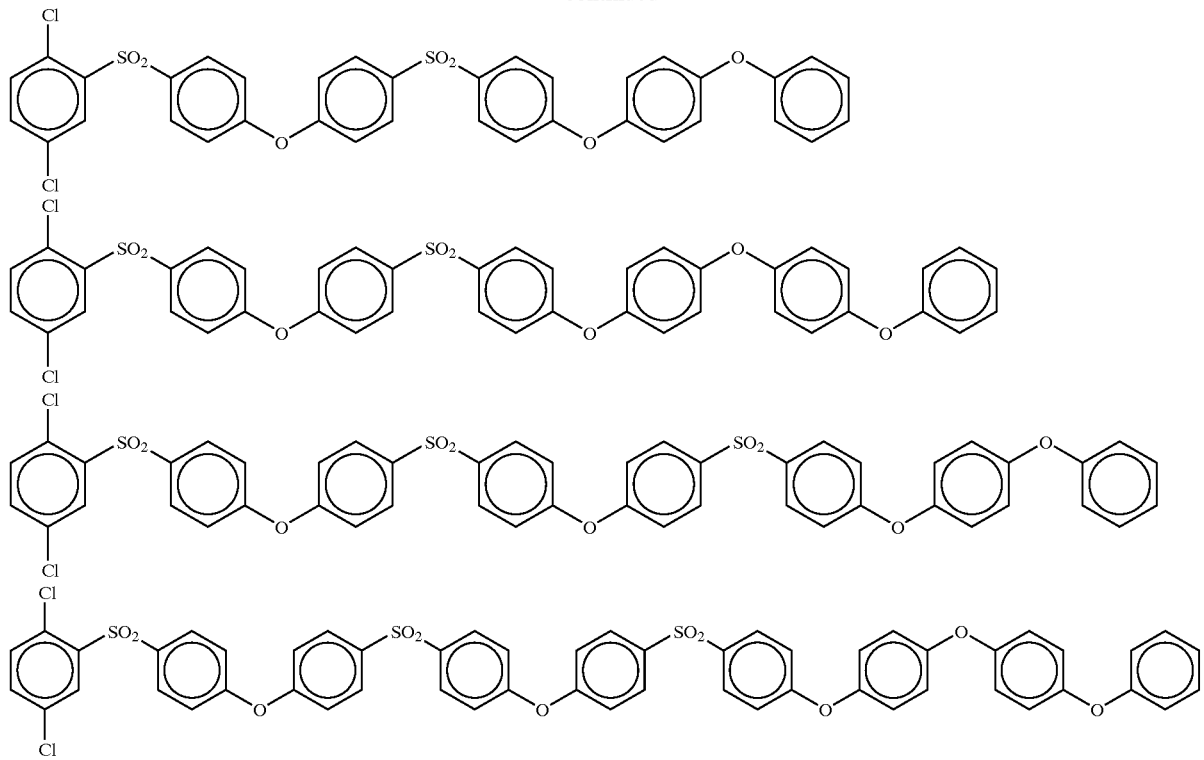

Of those, 2,5-dichloro-4'-[4-{4-(4-phenoxy)phenoxy}benzoyl]phenoxybenzo-phenone is particularly preferred because it realizes a high proton conductivity in a sulfonation product of the obtained (co)polymer, and even after sulfonation of the (co)polymer, the hot water resistance, mechanical strength, and oxidation resistance do not lower.

The monomer (B) can be synthesized by, for example, the following reactions.

The synthesis is constituted of the following three stages.

A) 2,5-Dichlorobenzoic acid is allowed to react with excessive diphenyl ether in the presence of a Lewis acid such as aluminum chloride by the Friedel-Crafts reaction.

B) 2,5-Dichloro-(4'-phenoxy)benzophone as obtained in the stage A) is allowed to react with 4-fluorobenzoic acid chloride by the Friedel-Crafts reaction.

C) F (fluorine) of the compound as obtained in the stage B) is allowed to react with 4-hydroxydiphenyl ether by nuclear substitution reaction.

These reactions are schematically illustrated below.

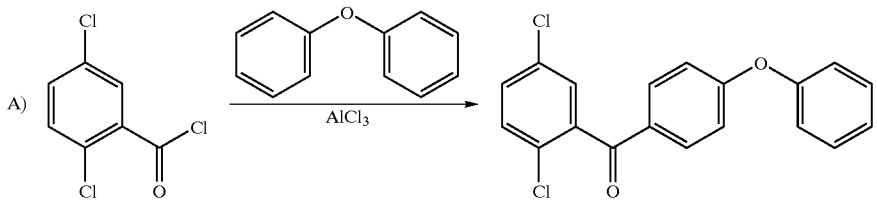

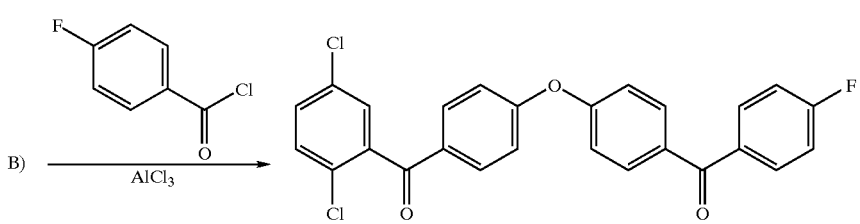

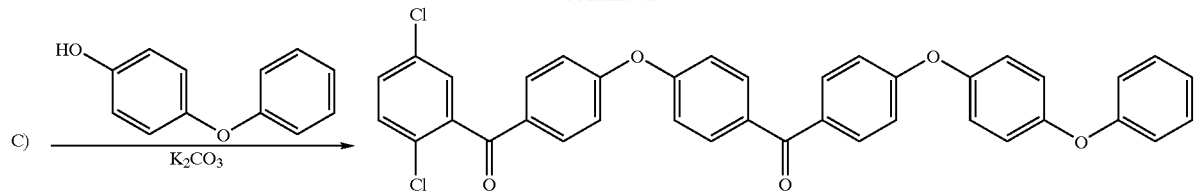

In the general formula (1bm), in the case of compounds wherein b is 2, in the reaction stage C), the following compound replaces the 4-hydroxydiphenyl ether.

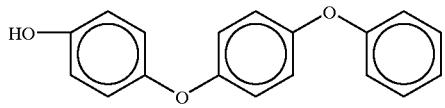

Further, in the case of compounds wherein b is more than 2, the following compound may replace the 4-hydroxydiphenyl ether.

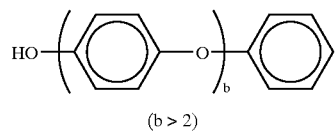

The compound to be reacted is obtained by the following nuclear substitution reaction.

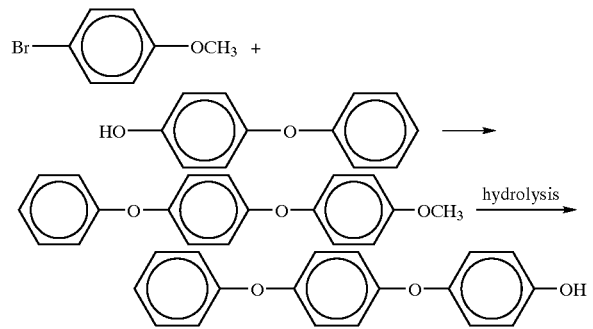

In addition, it is possible arbitrarily increase the number of benzene rings by repeating the nuclear substitution reaction and hydrolysis with the following compound.

In the general formula (1bm), in the case of compounds wherein a is 2, in the reaction stage A), the following compound replaces the diphenyl ether.

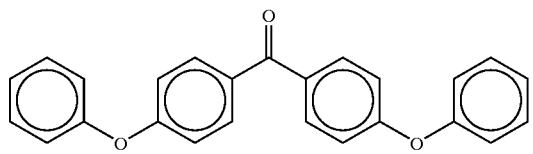

While the examples of the case where A is —O—, and B is >CO have been described, even in the case where A and B represent a different electron-withdrawing group and a different electron-donating group, respectively, the compounds can be synthesized by the same reaction stages.

The thus obtained monomer (B) of the invention can be identified for its structure by IR, NMR, and elemental analysis.

The halogenated aromatic compound represented by the general formula (1bm) that can be used in the invention can use monomers, oligomers, or polymers wherein a and/or b is more than 2, besides the monomers wherein a and b are each 1 or 2.

The resulting oligomer or polymer can be determined for its molecular weight by GPC, and the oligomer can be determined for its number average molecular weight by NMR.

Specific examples of the structure of the oligomer or polymer are shown below.

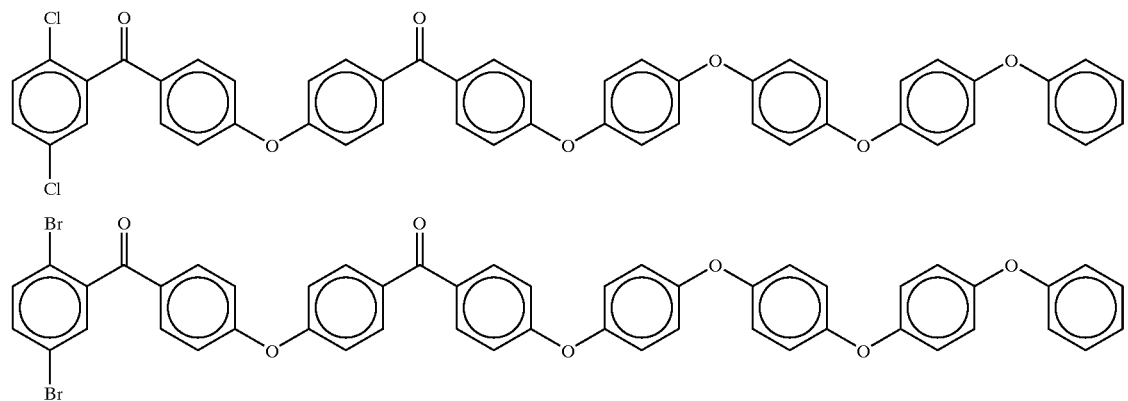

-continued
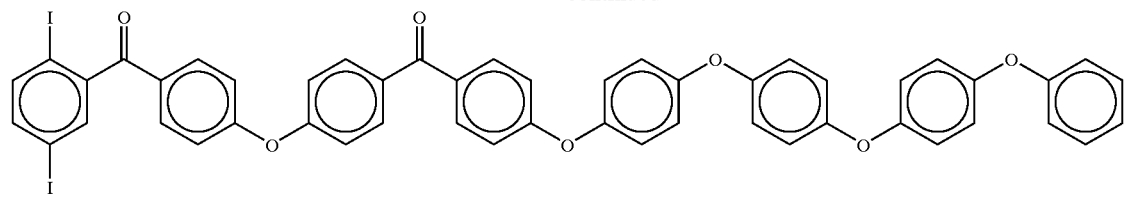
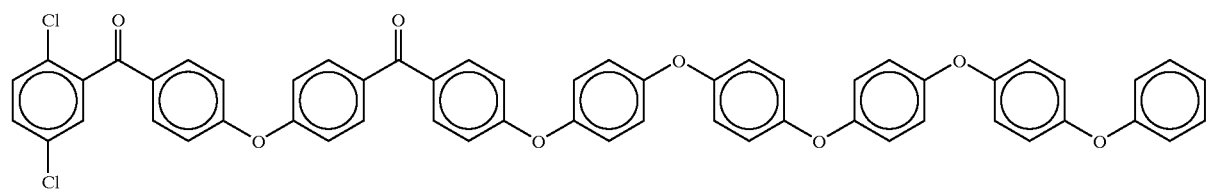
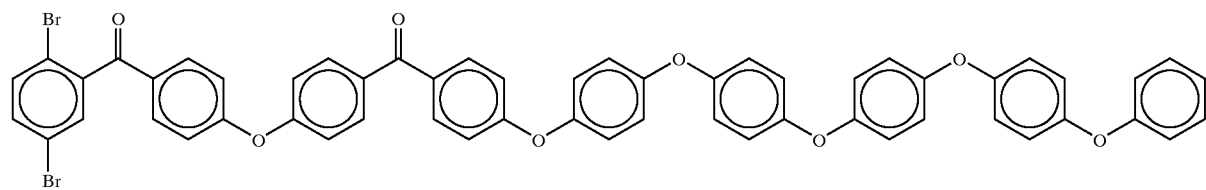
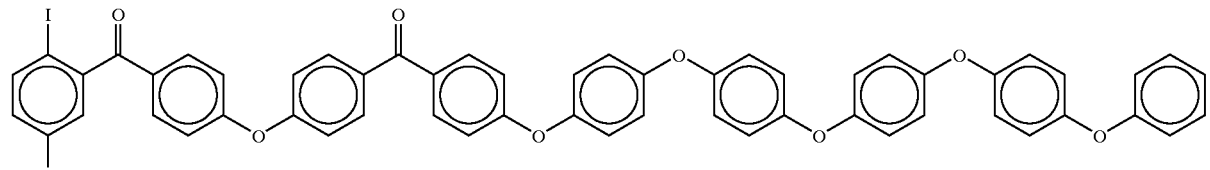
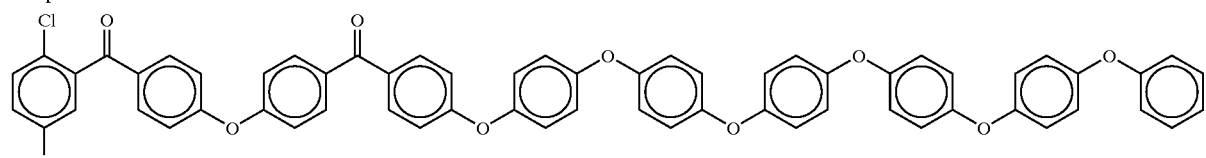
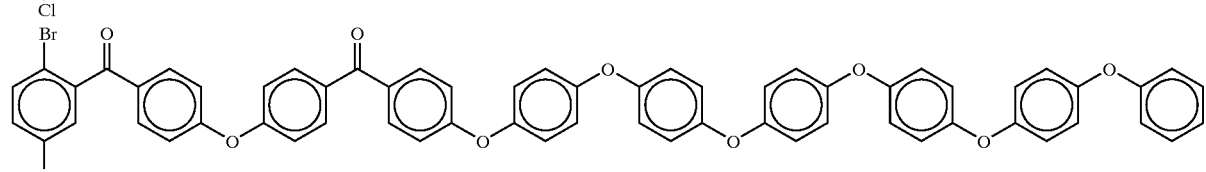
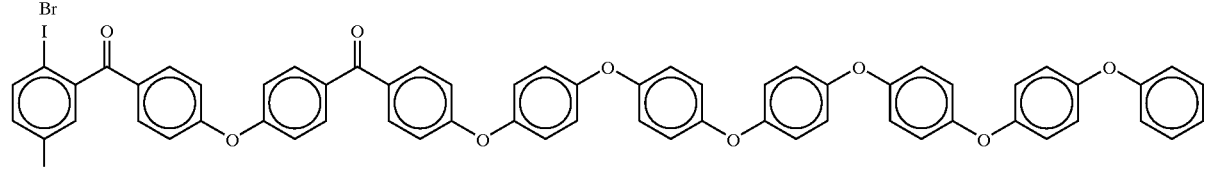
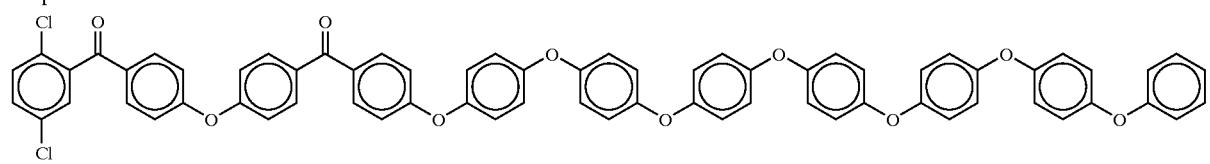
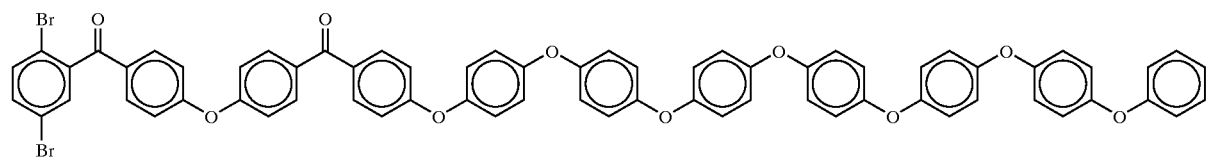

-continued

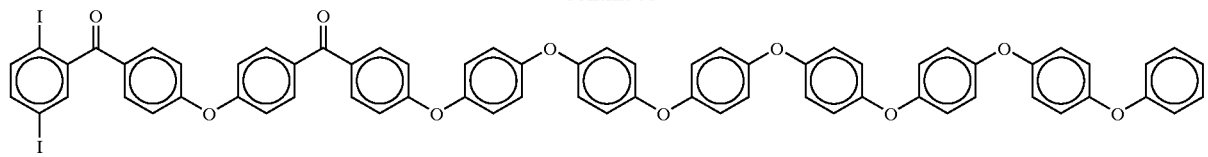

Polyarylene (Co)Polymer

The (co)polymer of the invention may be a homopolymer comprising only the repeating unit represented by the general formula (1b) (hereinafter referred to as "repeating unit (B)") or a copolymer comprising the repeating unit (B) and other repeating units. In any of these cases, the (co)polymer has a weight average molecular weight of from 10,000 to 1,000,000, and preferably from 20,000 to 800,000 as reduced into polystyrene (hereinafter simply referred to as "weight average molecular weight") as measured by gel permeation chromatography.

For example, when a sulfonated polymer obtained by sulfonation of a (co)polymer obtained by using as a monomer a compound represented by following formula (3):

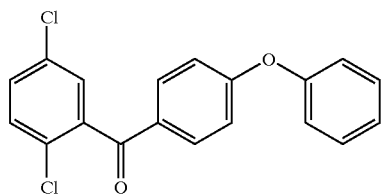

(3)

is compared with a sulfonated polymer obtained by sulfonation of a (co)polymer having the repeating unit (B) of the invention, even when the equivalence of the sulfonic acid groups as incorporated is equal, the sulfonated polymer according to the invention is higher in proton conductivity due to the localization of the sulfonated acid groups as incorporated in the side chains having higher molecular motion properties.

In the case where the (co)polymer has other repeating units, the content of the repeating unit (1b) is preferably from 5 to 99.9 mole % from the standpoint of enhancement of the sulfonic acid group activity.

In the case where the (co)polymer of the invention has repeating units other than the repeating unit (B) (hereinafter referred to as "other repeating units"), as the other repeating units, various units may be selected depending on the required properties and functions of polymer. In order to obtain a proton-conductive copolymer having good mechanical properties such as toughness, other repeating units represented by the general formula (1a) (hereafter generally referred to as "unit (A)") can be enumerated. The copolymer comprising the repeating unit (B) and the unit (A) can be sulfonated to produce a proton-conductive membrane material.

Examples of the monomer constituting the unit (A) (hereinafter referred to as "monomer (A)") include monomers represented by the following general formulae (1a-1m), (1a-2m) and (1a-3m), respectively (hereinafter referred to as "monomer (A1)", "monomer (A2)" and "monomer (A3)" in order).

Monomer (A1):

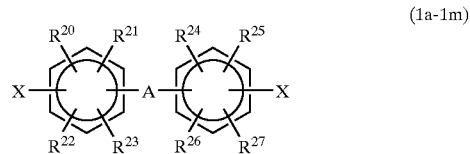

(1a-1m)

wherein Xs' independently represent a chlorine atom, a bromine atom, an iodine atom, or —$OSO_2Y$ (wherein Y represents an alkyl group, a halogenated alkyl group, or an aryl group); A represents the electron-withdrawing group as described for the general formula (1bm); and $R^{20}$ to $R^{27}$ are the same as defined in the general formula (1a).

Examples of the alkyl group include a methyl group and an ethyl group; and examples of the fluoroalkyl group include a trifluoromethyl group and a pentafluoroethyl group.

As to Y in the group represented by —$SO_2Y$, examples of the alkyl group include a methyl group and an ethyl group; examples of the halogenated alkyl group include a trifluoromethyl group and a pentafluoroethyl group; and examples of the aryl group include a phenyl group and a p-tolyl group.

Specific examples of the monomer (A1) are shown below.

(A1-1) 4,4'-dichlorobenzophenone, 2,4'-dichlorobenzophenone, 3,3'-dichloro-benzophenone, 4,4'-dibromobenzophenone, 2,4'-dibromobenzophenone, 3,3'-dibromobenzophenone, 4,4'-diiodobenzophenone, 2,4'-diiodobenzophenone, 3,3'-diiodobenzophenone, bis(4-trifluoromethylsulfonyloxyphenyl) ketone, bis(3-trilfuoromethylsulfonyloxyphenyl) ketone (A1-2) 4,4'-dichlorobenzanilide, 3,3'-dichlorobenzanilide, 3,4'-dichlorobenz-anilide, 4,4'-dibromobenzanilide, 3,3'-dibromobenzanilide, 3,4'-dibromobenzanilide, 4,4'-diiodobenzanilide, 3,3'-diiodobenzanilide, 3,4'-diiodobenzanilide (A1-3) bis(chlorophenyl)difluoromethane, bis(chlorophenyl)tetrafluoroethane, bis(chlorophenyl)hexafluoropropane, bis(chlorophenyl)octafluorobutane, bis(chloro-phenyl)decafluoropentane, bis(chlorophenyl)dodecafluorohexane, bis(chlorophenyl)tetradecafluoroheptane, bis(chlorophenyl)hexadecafluorooctane, bis(chlorophenyl)octadecafluorononane, bis(chlorophenyl)eicosafluorodecane, bis(bromophenyl)difluoromethane, bis(bromophenyl)tetrafluoroethane, bis(bromophenyl)hexafluoropropane, bis(bromophenyl)octafluorobutane, bis(bromophenyl)decafluoropentane, bis(bromophenyl)dodecafluorohexane, bis(bromophenyl)tetradecafluoroheptane, bis(bromophenyl)hexadecafluorooctane, bis(bromophenyl)octadecafluorononane, bis(bromophenyl)eicosafluorodecane, bis(iodophenyl)difluoromethane, bis(iodophenyl)tetrafluoroethane, bis(iodophenyl)hexafluoropropane, bis(iodophenyl)octafluorobutane, bis (iodophenyl)decafluoropentane, bis(iodophenyl) dodecafluorohexane, bis(iodophenyl) tetradecafluoroheptane, bis(iodophenyl) hexadecafluorooctane, bis(iodophenyl) octadecafluorononane, bis(iodophenyl)eicosafluorodecane (A1-4) 2,2-bis(4-chlorophenyl)hexafluoropropane, 2,2-bis(3-chlorophenyl)-hexafluoropropane, 2,2-bis(4-bromophenyl)hexafluoropropane, 2,2-bis(3-bromo-phenyl)hexafluoropropane, 2,2-bis(4-iodophenyl)hexafluoropropane, 2,2-bis(3-iodophenyl)hexafluoropropane, bis(4-trifluoromethylsulfonyloxyphenyl)hexafluoro-propane, bis(3-trifluoromethylsulfonyloxy phenyl)hexafluoropropane (A1-5) 4-chlorobenzoic acid-4-chlorophenyl, 4-chlorobenzoic acid-3-chlorophenyl, 3-chlorobenzoic acid-3-chlorophenyl, 3-chlorobenzoic acid-4-chlorophenyl, 4-bromobenzoic acid-4-bromophenyl, 4-bromobenzoic acid-3-bromophenyl, 3-bromobenzoic acid-3-bromophenyl, 3-bromobenzoic acid-4-bromophenyl (A1-6) bis(4-chlorophenyl) sulfoxide, bis(3-chlorophenyl) sulfoxide, bis(4-bromophenyl) sulfoxide, bis(3-bromophenyl) sulfoxide, bis(4-iodophenyl) sulfoxide, bis(3-iodophenyl) sulfoxide, bis(3-trifluoromethylsulfonyloxyphenyl) sulfoxide, bis(3-trifluoromphenyl) sulfonyloxyphenyl) sulfoxide (A1-7) bis(4-chlorophenyl) sulfone, bis(3-chlorophenyl) sulfone, bis(4-bromophenyl) sulfone, bis(3-bromophenyl) sulfone, bis(4-iodophenyl) sulfone, bis(3-iodophenyl) sulfone, bis(4-trifluoromethylsulfonyloxyphenyl) sulfone, bis(3-trifluoromethylsulfonyloxyphenyl) sulfone Monomer (A2):

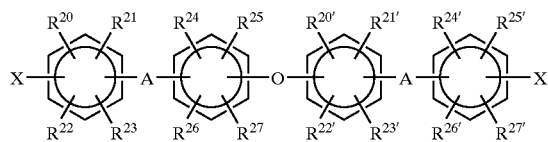

(1a-2m)

wherein $R^{20}$ to $R^{27}$ are as defined in the formula (1a-1m); As' independently represent the electron-withdrawing group as described for the general formula (1a-1m); and $R^{20}$ to $R^{27}$ are the same or different and each represents a hydrogen atom, a fluorine atom, an alkyl group, or a fluoroalkyl group.

In the general formula (1 a-2m), the alkyl group and the fluoroalkyl group are the same as defined in the general formula (1a-1m).

Specific examples of the monomer (A2) will be given below.

(A2-1) 4,4'-bis(4-chlorobenzoyl)diphenyl ether, 4,4'-bis(3-chlorobenzoyl)-diphenyl ether, 4,4'-bis(4-bromobenzoyl)diphenyl ether, 4,4-bis(3-bromobenzoyl)diphenyl ether, 4,4'-bis(4-iodobenzoyl)diphenyl ether, 4,4'-bis(3-iodobenzoyl)diphenyl ether, 4,4'-bis(4-trifluoromethylsulfonyloxyphenyl)diphenyl ether, 4,4'-bis(3-trifluoromethylsulfonyloxyphenyl)diphenyl ether, 4,4'-bis(4-methyl-sulfonyloxyphenyl)diphenyl ether, 4,4'-bis(3-methylsulfonyloxyphenyl)diphenyl ether (A2-2) 4,4'-bis(4-chlorobenzoylamino)diphenyl ether, 3,4'-bis(4-chloro-benzoylamino)diphenyl ether, 4,4'-bis(3-chlorobenzoylamino)diphenyl ether, 3,4'-bis(3-chlorobenzoylamino)diphenyl ether, 4,4'-bis(4-bromobenzoylamino)diphenyl ether, 3,4'-bis(4-bromobenzoylamino)diphenyl ether, 3,4'-bis(4-bromobenzoylamino)-diphenyl ether, 4,4'-bis(4-bromobenzoylamino)diphenyl ether, 3,4'-bis(3-bromobenzoylamino)diphenyl ether, 4,4'-bis(4-iodobenozylamino)diphenyl ether, 3,4'-bis(4-iodobenzoylamino)diphenyl ether, 4,4'-bis(3-iodobenzoylamino)diphenyl ether, 3,4'-bis(3-iodobenzoylamino)diphenyl ether, 4,4'-bis(4-trifluoromethylsulfonyl-oxyphenyl)diphenyl ether, 3,4'-bis(4-trifluoromethylsulfonyloxyphenyl)diphenyl 4,4'-bis(3-trifluoromethylsulfonyloxyphenyl)diphenyl ether, 3,4'-bis(3-trifluoromethyl-sulfonyloxyphenyl)diphenyl ether, 4,4'-bis(4-methylsulfonyloxyphenyl)diphenyl ether, 3,4'-bis(4-methylsulfonyloxyphenyl)diphenyl ether, 4,4'-bis(3-methylsulfonyloxy-phenyl)diphenyl ether, 3,4'-bis(3-methylsulfonyloxyphenyl)diphenyl ether (A2-3) 4,4'-bis(4-chlorophenylsulfonyl)diphenyl ether, 3,4'-bis(4-chloro-phenylsulfonyl) diphenyl ether, 4,4'-bis(3-chlorophenylsulfonyl)diphenyl ether, 3,4'-bis(3-chlorophenylsulfonyl)diphenyl ether, 4,4'-bis(4-bromophenylsulfonyl)-diphenyl ether, 3,4'-bis(4-bromophenylsulfonyl)diphenyl ether, 4,4'-bis(3-bromophenylsulfonyl) diphenyl ether, 3,4'-bis(3-bromophenylsulfonyl)-diphenyl ether, 4,4'-bis(4-iodophenylsulfonyl)diphenyl ether, 3,4'-bis(4-iodophenylsulfonyl)diphenyl ether, 4,4'-bis(3-iodophenylsulfonyl)diphenyl ether, 3,4'-bis(3-iodophenylsulfonyl)diphenyl ether, 4,4'-bis(4-trifluoromethylsulfonyloxyphenylsulfonyl)diphenyl ether, 3,4'-bis(4-trifluoromethyl sulfonyloxy-phenylsulfonyl) diphenyl ether, 4,4'-bis(3-trifluoromethylsulfonyloxy phenyl-sulfonyl)diphenyl ether, 3,4'-bis(3-trifluoromethylsulfonyloxyphenylsulfonyl)diphenyl ether, 4,4'-bis(4-methylsulfonyloxyphenylsulfonyl)diphenyl ether, 3,4'-bis(4-methylsulfonyloxy-phenylsulfonyl)diphenyl ether, 4,4'-bis(3-methylsulfonyloxyphenylsulfonyl)diphenyl ether, 3,4'-bis(3-methylsulfonyloxyphenylsulfonyl)diphenyl ether (A2-4) 4,4'-bis(4-chlorophenyl)diphenyl ether dicarboxylate, 3,4'-bis(4-chlorophenyl)diphenyl ether dicarboxylate, 4,4'-bis(3-chlorophenyl)diphenyl ether dicarboxylate, 3,4'-bis(3-chlorophenyl)diphenyl ether dicarboxylate, 4,4'-bis(4-bromophenyl)diphenyl ether dicarboxylate, 3,4'-bis(4-bromophenyl)diphenyl ether dicarboxylate, 4,4'-bis(3-bromophenyl)diphenyl ether dicarboxylate, 3,4'-bis(3-bromophenyl)diphenyl ether dicarboxylate, 4,4'-bis(4-iodophenyl)diphenyl ether dicarboxylate, 3,4'-bis(4-iodophenyl)diphenyl ether dicarboxylate, 4,4'-bis(3-iodophenyl)diphenyl ether dicarboxylate, 3,4'-bis(3-iodophenyl)diphenyl ether dicarboxylate, 4,4'-bis(4-trifluoromethylsulfonyloxyphenyl) diphenyl ether dicarboxylate, 3,4'-bis(4-trifluoromethylsulfonyloxyphenyl)diphenyl ether dicarboxylate, 4,4'-bis(3-trifluoromethylsulfonyloxyphenyl) diphenyl ether dicarboxylate, 3,4'-bis(3-trifluoromethylsulfonyloxyphenyl) diphenyl ether dicarboxylate, 4,4'-bis(4-methylsulfonyloxyphenyl) diphenyl ether dicarboxylate, 3,4'-bis(4-methylsulfonyloxyphenyl)diphenyl ether dicarboxylate, 4,4'-bis(3-methylsulfonyloxyphenyl)diphenyl ether dicarboxylate, 3,4'-bis(3-methylsulfonyloxyphenyl) diphenyl dicarboxylate (A2-5) 4,4 '-bis [(4-chlorophenyl)- 1,1,1,3,3,3-hexafluoropropyl]diphenyl ether, 3,4'-bis[(4-chlorophenyl)-1,1,1,3,3,3-hexafluoropropyl]diphenyl ether, 4,4'-bis[(3-chlorophenyl)-1,1,1,3,3,3-hexafluoropropyl]diphenyl ether, 3,4'-bis[(3-chlorophenyl)-1,1,1,3,3,3-hexafluoropropyl] diphenyl ether, 4,4'-bis[(4-bromophenyl)-1,1,1,3,3,3-hexafluoropropyl]diphenyl ether, 3,4'-bis[(4-bromophenyl)-1,1,1,3,3,3-hexafluoropropyl]diphenyl ether, 4,4'-bis[(3- bromophenyl)-1,1,1,3,3,3-hexafluoropropyl]diphenyl ether, 3,4'-bis[(3-bromophenyl)-1,1,1,3,3,3-hexafluoropropyl] diphenyl ether, 4,4'-bis[(4-iodophenyl)-1,1,1,3,3,3-hexafluoropropyl]diphenyl ether, 3,4'-bis[(4-iodophenyl)-1,1,1,3,3,3-hexafluoropropyl]diphenyl ether, 4,4'-bis[(3-iodophenyl)-1,1,1,3,3,3-hexafluoropropyl]diphenyl ether, 3,4'-bis[(3-iodophenyl)-1,1,1,3,3,3-hexafluoropropyl] diphenyl ether, 4,4'-bis[(4-trifluoromethylsulfonyloxyphenyl)-1,1,1,3,3,3-hexafluoropropyl]diphenyl ether, 3,4'-bis-[(4-trifluoromethylsulfonyloxyphenyl)-1,1,1,3,3,3-hexafluoropropyl]diphenyl ether, 4,4'-bis[(3-trifluoromethylsulfonyloxyphenyl)- 1,1,1,3,3,3-hexafluoropropyl]diphenyl ether, 3,4'-bis[(3-trifluoromethylsulfonyloxyphenyl)-1,1,1,3,3,3-hexafluoropropyl]-diphenyl ether, 4,4'-bis[(4-methylsulfonyloxyphenyl)-1,1,1,3,3,3- hexafluoropropyl]-diphenyl ether, 3,4 '-bis [(4-methylsulfonyloxyphenyl)- 1,1,1,3,3 ,3-hexafluoropropyl]-diphenyl ether, 4,4'-bis[(3-methylsulfonyloxyphenyl)-1,1,1,3,3,3-hexafluoropropyl]-diphenyl ether, 3,4'-bis[(3-methylsulfonyloxyphenyl)-1,1,1,3,3,3-hexafluoropropyl]-diphenyl ether (A2-6) 4,4'-bis[(4-chlorophenyl)tetrafluoroethyl]diphenyl ether, 4,4'-bis[(3-chlorophenyl)tetrafluoroethyl]diphenyl ether, 4,4'-bis[(4-chlorophenyl)hexafluoro-propyl]diphenyl ether, 4,4'-bis[(3-chlorophenyl)hexafluoropropyl]diphenyl ether, 4,4'-bis[(4-chlorophenyl)octafluorobutyl]diphenyl ether, 4,4'-bis[(3-chlorophenyl)-octafluorobutyl]diphenyl ether, 4,4'-bis[(4-chlorophenyl)decafluoropentyl]diphenyl ether, 4,4'-bis[(3-chlorophenyl)decafluoropentyl]diphenyl ether, 4,4'-bis[(4-bromo-phenyl)tetrafluoroethyl]diphenyl ether, 4,4'-bis[(3-bromophenyl)tetrafluoroethyl]-diphenyl ether, 4,4'-bis[(4-bromophenyl)hexafluoropropyl]diphenyl ether, 4,4'-bis[(3-bromophenyl)hexafluoropropyl]diphenyl ether, 4,4'-bis[(4-bromophenyl)octafluoro-butyl]diphenyl ether, 4,4'-bis[(3-bromopheny)octafluorobutyl]diphenyl ether, 4,4'-bis[(4-bromophenyl)decafluoropentyl]diphenyl ether, 4,4'-bis[(3-bromophenyl)-decafluoropentyl]diphenyl ether, 4,4'-bis[(4-iodophenyl)tetrafluoroethyl]diphenyl ether, 4,4'-bis[(3-iodophenyl)tetrafluoroethyl]diphenyl ether, 4,4'-bis[(4-iodophenyl)-hexafluoropropyl]diphenyl ether, 4,4'-bis[(3-iodophenyl)hexafluoropropyl]diphenyl ether, 4,4'-bis[(4-iodophenyl)octafluorobutyl]diphenyl ether, 4,4'-bis[(3-iodophenyl)-octafluorobutyl]diphenyl ether, 4,4'-bis[(4-iodophenyl)decafluoropentyl]diphenyl ether, 4,4'-bis[(3-iodophenyl)decafluoropentyl]diphenyl ether, 4,4'-bis[(4-trifluoromethyl-sulfonyloxyphenyl)tetrafluoroethyl]diphenyl ether, 4,4'-bis[(3-trifluoromethyl-sulfonyloxyphenyl)tetrafluoroethyl]diphenyl ether, 4,4'-bis[(4-trifluoromethyl-sulfonyloxyphenyl)hexafluoropropyl] diphenyl ether, 4,4'-bis[(3-trifluoromethyl-sulfonyloxyphenyl)hexafluoropropyl]diphenyl ether, 4,4'-bis[(4-trifluoromethyl-sulfonyloxyphenyl)octafluorobutyl] diphenyl ether, 4,4'-bis[(3-trifluoromethylsulfonyl-oxyphenyl)octafluorobutyl]diphenyl ether, 4,4'-bis[(4-trifluoromethylsulfonyloxy-phenyl)decafluoropentyl] diphenyl ether, 4,4'-bis[(3-trifluoromethyl-sulfonyloxy) decafluoropentyl]diphenyl ether, 4,4'-bis[(4-methylsulfonyloxyphenyl)-tetrafluoroethyl]diphenyl ether, 4,4'-bis[(3-methylsulfonyloxyphenyl)tetra-fluoroethyl] diphenyl ether, 4,4'-bis[(4-methylsulfonyloxyphenyl)-hexafluoropropyl]diphenyl ether, 4,4'-bis[(3-methylsulfonyloxyphenyl)hexafluoro-propyl]diphenyl ether, 4,4'-bis[(4-methylsulfonyloxyphenyl)octafluorobutyl] diphenyl ether, 4,4'-bis[(3-methylsulfonyloxypheny) octafluorobutyl]diphenyl ether, 4,4'-bis[(4-methylsulfonyloxyphenyl)decafluoropentyl]diphenyl ether, 4,4'-bis[(3-methylsulfonyl-oxy)decafluoropentyl]diphenyl ether Monomer (A3):

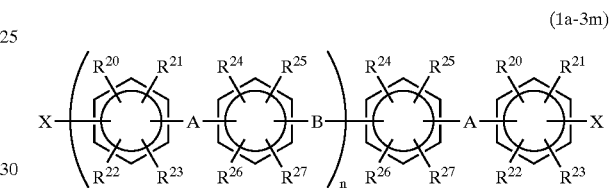

(1a-3m)

wherein As' independently represent an electron-withdrawing group as defined in the general formula (1a-1m); Bs' independently represent an electron-donating atom or divalent group as defined for the general formula (1bm); Xs' independently represent a chlorine atom, a bromine atom, or an iodine atom; $R^{20}$ to $R^{27}$ are the same as defined in the general formula (1a); and n represents an integer of 2 or more, preferably from 2 to 100, and more preferably from 2 to 80.

Specific examples of the monomer (A3) include 2,2-bis [4-{4-(4-chlorobenzoyl)phenoxy}phenyl]-1,1,1,3,3,3-hexafluoropropane, bis[4- {4-(4-chlorobenzoyl) phenoxy}phenyl]sulfone, and compounds represented by the following chemical formulae.

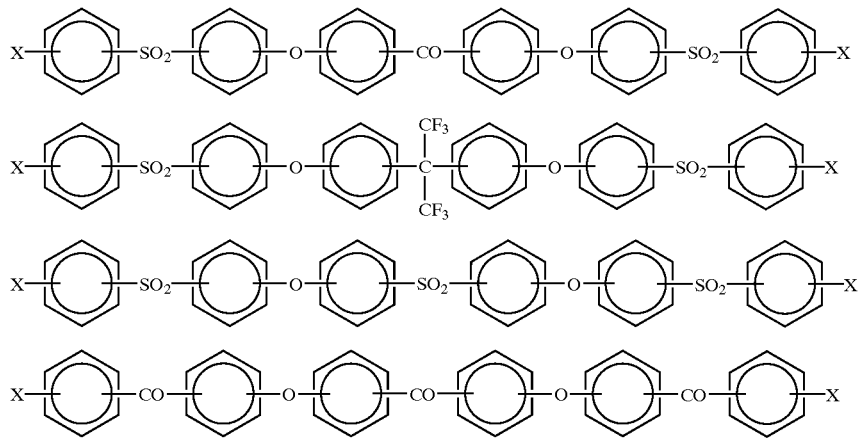

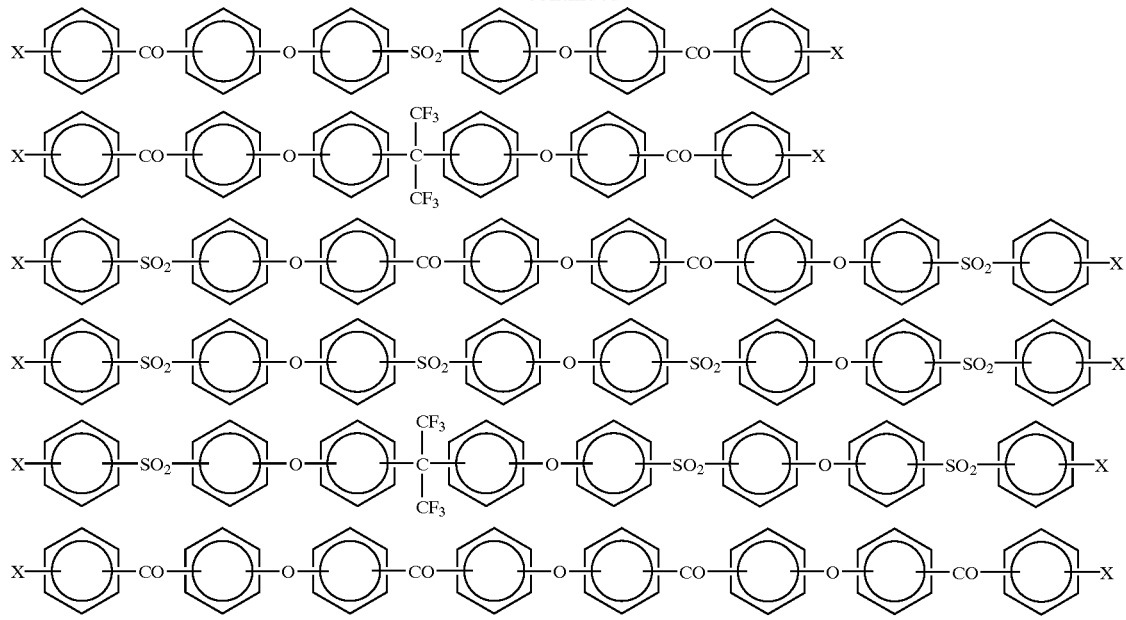

In the abovegeneral formulae, X is the same as defined in the general formula (1a-3m).

As the monomer (A3) that can be used in the invention, not only monomers wherein n represents 2, but also oligomers or polymers wherein n represents more than 2 can be used.

Specific examples of the structural formulae of the oligomers or polymers having an aromatic chloride in the molecular terminal ends thereof are shown below.

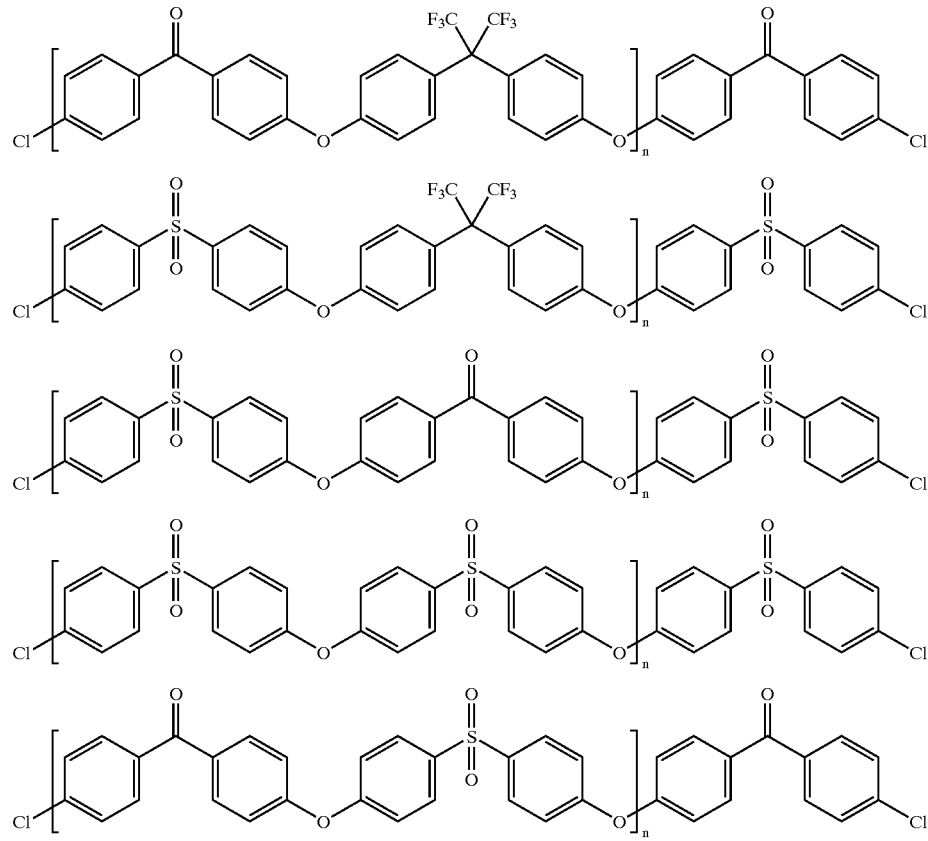

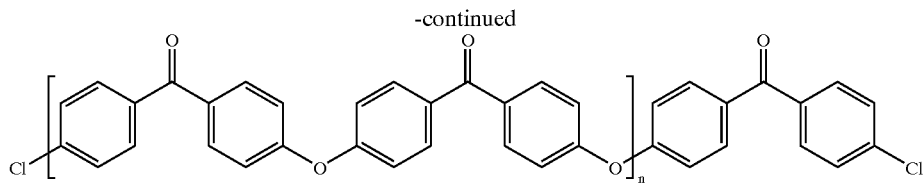

For example, in the case where the electron-donating group is —O—, the monomer (A3) can be synthesized by reaction of a bisphenol having the electron-withdrawing group A connected thereto with an electron-withdrawing group-activated aromatic dihalide having a halogen atom (such as fluorine and chlorine) substituted thereon, such as 4,4'-difluorobenzophenone, 4,4'-dichlorobenzophenone, 4,4'-chlorofluoro-benzophene, bis(4-chlorophenyl) sulfone, bis(4-fluorophenyl) sulfone, 4-fluorophenyl-4'-chlorophenyl sulfone, bis(3-nitro-4-chlorophenyl) sulfone, 2,6-dichlorobenzonitrile, 2,6-difluorobenzonitrile, hexafluorobenzene, decafluorobiphenyl, 2,5-difluorobenzophenone, and 1,3-bis(4-chlorobenzoyl) benzene. For obtaining the desired activated chlorine-terminated compound, it is preferred to use as the active aromatic dihalide a chlorofluoro compound having each one of halogen atoms having different reactivity because the fluorine atom preferentially causes a nuclear substitution reaction with the phenoxide as shown in the following reaction scheme.

ferred. These compounds as the ligand component can be used singly or in combination of two or more thereof.

Examples of the transition metal complex having a ligand previously coordinated therein include nickel chloride bis(triphenylphosphine), nickel bromide bis(triphenylphosphine), nickel iodide bis(triphenylphosphine), nickel nitrate bis(triphenylphosphine), nickel chloride(2,2'-bipyridine), nickel bromide(2,2'-bipyridine), nickel iodide (2,2'-bipyridine), nickel nitrate(2,2'-bipyrdine), bis(1,5-cyclooctadiene)nickel, tetrakis(triphenylphosphine)nickel, tetrakis(triphenylphosphite)nickel, and tetrakis(triphenylphosphine)palladium, with nickel chloride bis(triphenylphosphine) and nickel chloride(2,2'-bipyridine) being preferred.

Examples of the reducing agent that can be used in the catalyst system include iron, zinc, manganese, aluminum, magnesium, sodium, and calcium, with zinc, magnesium, and manganese being preferred. These reducing agents can be activated and then used upon contact with an acid such as organic acids.

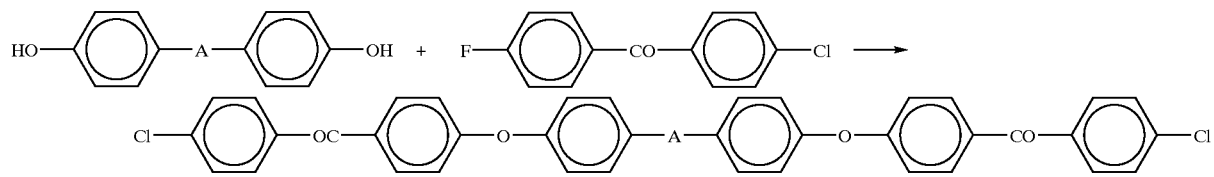

Synthesis of Polyarylene (Co)Polymer

The polyarylene homopolymer of the invention can be synthesized by coupling polymerization of the monomer (B); and the polyarylene copolymer of the invention can be synthesized by coupling reaction of the monomer (B) with the monomer (A), respectively.

The catalyst to be used in the production of the polyarylene (co)polymer of the invention is a catalyst containing a transition metal compound. This catalyst system comprises as essential components (1) a transition metal salt and a compound as a ligand (hereinafter referred to as "ligand component") or a transition metal complex (including a copper salt) having a ligand coordinated therein and (2) a reducing agent. In order to further increase the polymerization speed, the catalyst system may contain a "salt".

Examples of the transition metal salt employable herein include nickel compounds such as nickel chloride, nickel bromide, nickel iodide, and nickel acetylacetonate; palladium compounds such as palladium chloride, palladium bromide, and palladium iodide; iron compounds such as iron chloride, iron bromide, and iron iodide; and cobalt compounds such as cobalt chloride, cobalt bromide, and cobalt iodide. Of those, nickel chloride and nickel bromide are particularly preferable.

Examples of the ligand component employable herein include triphenyl phosphine, 2,2'-bipyridine, 1,5-cyclooctadiene, and 1,3-bis(diphenylphosphino)propane, with triphenyl phosphine and 2,2'-bipyridine being pre- Examples of the "salt" that can be used in the catalyst system include sodium compounds such as sodium fluoride, sodium chloride, sodium bromide, sodium iodide, and sodium sulfate; potassium compounds such as potassium fluoride, potassium chloride, potassium bromide, potassium iodide, and potassium sulfate; and ammonium compounds such as tetraethylammonium fluoride, tetraethylammonium chloride, tetraethylammonium bromide, tetraethylammonium iodide, and tetraethylammonium sulfate, with sodium bromide, sodium iodide, potassium bromide, tetraethylammonium bromide, and tetraethylammonium iodide being preferred.

With respect to the proportion of the respective components to be used in the catalyst system, the proportion of the transition metal salt or transition metal complex is usually from 0.0001 to 10 moles, and preferably from 0.01 to 0.5 moles, per mole of the total amount of the monomers. When the proportion of the transition metal salt or transition metal complex is less than 0.0001 moles, the polymerization reaction does not proceed sufficiently. On the other hand, when it exceeds 10 moles, there is a problem that the molecular weight of the resulting (co)polymer is lowered.

In the case where the catalyst system comprises a transition metal salt and a ligand component, the proportion of the ligand component is usually from 0.1 to 100 moles, and preferably from 1 to 10 moles, per mole of the transition metal salt. When the proportion of the ligand component is less than 0.1 moles, the catalytic activity is insufficient. On the other had, when it exceeds 100 moles, there is a problem that the molecular weight of the resulting (co)polymer is lowered.

The proportion of the reducing agent to be used in the catalyst system is usually from 0.1 to 100 moles, and preferably from 1 to 10 moles per mole of the total amount of the monomers. When the proportion of the reducing agent is less than 0.1 moles, the polymerization does not proceed sufficiently. On the other hand, when it exceeds 100 moles, there is a problem that the purification of the resulting (co)polymer becomes difficult.

In the case where the "salt" is used in the catalyst system, the proportion of the "salt" to be used is usually from 0.001 to 100 moles, and preferably from 0.01 to 1 mole per mole of the total amount of the monomers. When the proportion of the "salt" is less than 0.001 moles, the effect of increasing the polymerization speed is insufficient. On the other hand, when it exceeds 100 moles, there is a problem that the purification of the resulting (co)polymer becomes difficult.

Examples of the polymerization solvent that can be used for the synthesis of the polyarylene (co)polymer include tetrahydrofuran, cyclohexanone, dimethyl sulfoxide, N,N-dimethylformamide, N,N-dimethylacetamide, N-methyl-2-pyrrolidone, γ-butyrolactone, and γ-butyrolactam, with tetrahydrofuran, N,N-dimethylformamide, N,N-dimethylacetamide, and N-methyl-2-pyrrolidone being preferred. Preferably, the polymerization solvent is used after thoroughly drying.

A total concentration of the monomers in the polymerization solvent is usually from 1 to 90% by weight, and preferably from 5 to 40% by weight.

A polymerization temperature at which the polyarylene (co)polymer is produced is usually from 0 to 200° C., and preferably from 50 to 120° C. A polymerization time is usually from 0.5 to 100 hours, and preferably from 1 to 40 hours.

For example, the monomer (A3) and the monomer (B) are subjected to polymerization under the foregoing conditions to obtain a copolymer represented by the following general formula.

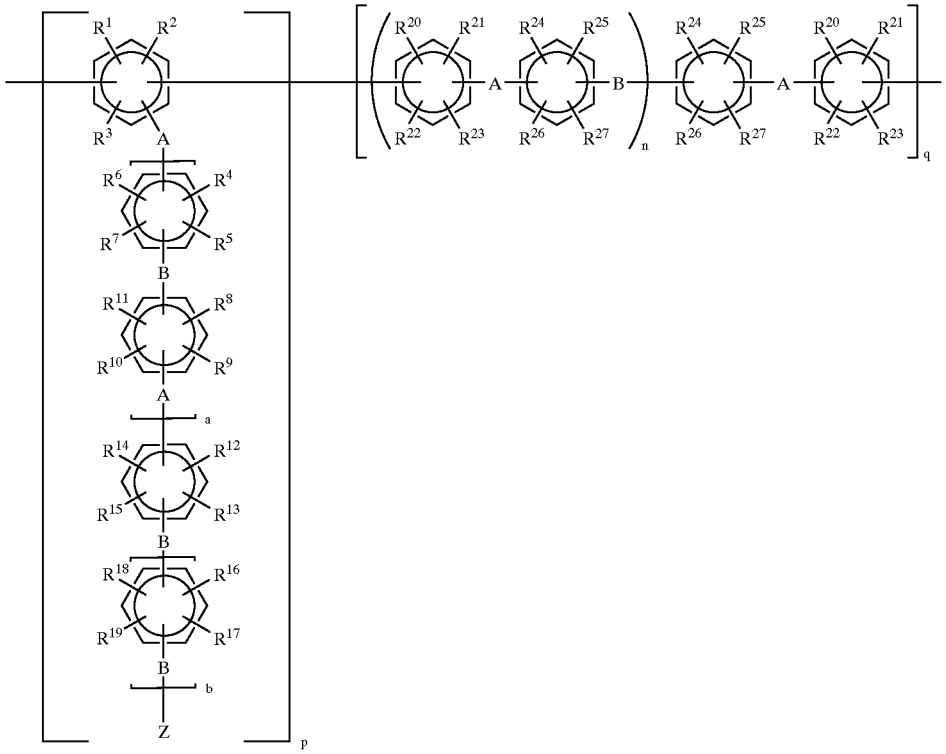

wherein A, B, Z, $R^1$ to $R^{27}$, a, b, and n are the same as defined above; p and q each independently represents the number of the respective repeating units, provided that a ratio of p to q (i.e., a molar ratio of the two repeating units) is from 5/95 to 99.9/0.1, and preferably from 5/95 to 99/1.

The structure of the polyarylene (co)polymer can be confirmed by, for example, C—O—C absorption at from 1,230 to 1,250 cm$^{-1}$ or C=O absorption at from 1,640 to 1,660 cm$^{-1}$ on infrared absorption spectrum. Also, the structure of the polyarylene (co)polymer can be confirmed by the peak of aromatic protons of from 6.8 to 8.0 ppm on nuclear magnetic resonance spectrum ($^1$H-NMR).

Sulfonation of Polvarylene (Co)Polymer

The (co)polymer having a sulfonic acid group can be obtained by incorporating a sulfonic acid group into the foregoing sulfonic acid group-free (co)polymer using a sulfonating agent in a customary manner.

In order to incorporate a sulfonic acid group into the sulfonic acid group-free (co)polymer, the foregoing sulfonic acid group-free (co)polymer can be sulfonated by using a known sulfonating agent such as sulfuric anhydride, fuming sulfuric acid, chlorosulfonic acid, sulfuric acid, and sodium hydrogensulfite under known conditions in the absence or presence of a solvent.

Examples of the solvent include hydrocarbon solvents such as n-hexane; ether-based solvents such as tetrahydrofuran and dioxane; aprotic polar solvents such as dimethylacetamide, dimethylformamide, and dimethyl sulfoxide; and halogenated hydrocarbons such as tetrachloroehtane, dichloroethane, chloroform, and methylene chloride. The reaction temperature is not particularly limited but is usually from −50 to 200° C., and preferably from −10 to 100° C. Further, the reaction time is usually from 0.5 to 1,000 hours, and preferably from 1 to 200 hours.

The amount of the sulfonic acid group in the sulfonic acid group-containing (co)polymer of the invention thus obtained is from 0.5 to 3 meq./g, and preferably from 0.8 to 2.8 meq./g. When the amount of the sulfonic acid group is less than 0.5 meq./g, the proton conductivity of the resulting (co)polymer does not increase. On the other hand, when it exceeds 3 meq./g, the hydrophilicity of the resulting (co)polymer increases, whereby the (co)polymer becomes a water-soluble polymer, or though the (co)polymer does not become water-soluble, its durability is lowered.

The amount of the sulfonic acid group can be easily adjusted by changing the kind of the monomer (B), or in the case of the copolymer, by changing the kinds and combination of the monomer (A) and the monomer (B).

The molecular weight of an unsulfonated precursor polymer of the sulfonic acid group-containing polyarylene (co)polymer thus obtained is from $10 \times 10^3$ to $1,000 \times 10^3$, and preferably from $20 \times 10^3$ to $800 \times 10^3$, in terms of weight average molecular weight as reduced into polystyrene. When the molecular weight of the unsulfonated precursor polymer is less than $10 \times 10^3$, the unsulfonated precursor polymer exhibits insufficient coatability so that the film thus formed generates cracks and exhibits an insufficient strength. On the other hand, when it exceeds $1,000 \times 10^3$, the unsulfonated precursor polymer exhibits insufficient solubility and a high solution viscosity and hence, becomes poor in processability.

The structure of the sulfonic acid group-containing (co)polymer can be confirmed by, for example, S=O absorption at from 1,030 to 1,045 cm$^{-1}$ and from 1,160 to 1,190 cm$^{-1}$, C—O—C absorption at from 1,130 to 1,250 cm$^{-1}$, or C=O absorption at from 1,640 to 1,660 cm$^{-1}$ on infrared absorption spectrum. The composition ratio of theses components can be determined by neutralization titration of sulfonic acid or elemental analysis. Further, the structure of the (co)polymer can be confirmed by the peak of aromatic protons of from 6.8 to 8.0 ppm on nuclear magnetic resonance spectrum ($^1$H-NMR).

Proton-Conductive Membrane

The proton-conductive membrane of the invention is made of the sulfonic acid group-containing (co)polymer. But, the proton-conductive membrane may further comprise an inorganic acid such as sulfuric acid and phosphoric acid, an organic acid such as carboxylic acids, and a proper amount of water, in combination with the sulfonic acid group-containing (co)polymer.

In order to produce the conductive membrane of the invention, for example, the sulfonic acid group-containing (co)polymer of the invention may be dissolved in a solvent and then subjected to a casting method including casting for making a film or a melt forming method.

Examples of the solvent that is used in the casting method include aprotic polar solvents such as dimethylacetamide, dimethylformamide, N-methyl-2-pyrrolidone, and dimethyl sulfoxide. These solvents may be further mixed with an alcohol solvent such as methanol.

The conductive membrane of the invention can be used as, for example, a proton-conductive membrane for primary battery electrolyte, secondary batter electrolyte, fuel cell polymer solid electrolyte, display element, various sensors, signal medium, solid capacitor, or ion exchange membrane.

The invention will be further described in detail with reference to the following Examples, but it should not be construed that the invention is limited thereto.

The evaluation of various measurement items in the Examples was made in the following manners.

Weight Average Molecular Weight:

The weight average molecular weight of the unsulfonated precursor polymer was determined in terms of molecular weight as reduced into polystyrene using tetrahydrofuran as a solvent by gel permeation chromatography (GPC).

Amount of Sulfonic Acid Group:

The sulfonated polymer thus obtained was washed with water until the wash water exhibited a pH of from 4 to 6, thereby removing the remaining free acid. Thereafter, the sulfonated polymer was thoroughly washed with water, dried, and then weighed in a predetermined amount. The resulting sulfonated polymer was dissolved in a mixed solvent of THF and water. The solution was then neutralized with a standard NaOH solution while using phenolphthalein as an indicator. From the neutralization point, the amount of the sulfonic acid group (mg-equivalent/g) was determined.

Proton Conductivity:

Platinum wires (diameter: 0.5 mm) were pressed against the surface of a 5 mm wide strip-shaped film specimen and kept in a constant temperature and humidity device, thereby measuring an alternating current impedance across the platinum wires, from which was then determined an alternating current resistivity. The impedance was measured at an alternating current of 10 kHz under a circumstance at 85° C. and at a relative humidity of 90%.

A chemical impedance measurement system produced by NF Corporation was used as the resistivity measurement device. JW241, produced by Yamato Chemical Co., Ltd., was used as the constant temperature and humidity device. Five platinum wires were pressed against the surface of the test specimen at an interval of 5 mm. The alternating current resistivity was measured by changing the distance between the electrodes from 5 to 20 mm.

The distance between the electrodes and the resistivity gradient were then substituted in the following equation to calculate the specific resistivity of the film. The reciprocal of the specific resistivity was then calculated to determine the alternating current impedance (proton conductivity [S/cm]= 1/[Ω·cm].

(Specific resistivity [Ω·cm])=0.5 [cm]×(film thickness [cm])×(resistivity gradient between electrodes [Ω/cm])

Tensile Strength Properties:

A test specimen was prepared by forming a 50 μm-thick sulfonated polymer film having a size of 3 mm (in width)×65 mm (in length) (distance between chucks: 25 mm). Using a tensile testing machine, the test specimen was measured for elastic modulus, breaking strength, yield strength, and elongation at room temperature.

Hot Water Resistance:

The film was dipped in hot water at 95° C. When the film exhibited a weight retention after dipping of 90% or more, it was evaluated "good", whereas when the weight retention after dipping was less than 90%, the film was evaluated "poor".

Resistance to Fenton's Reagent:

The film sample was dipped in an aqueous solution at 40° C. containing 3% of hydrogen peroxide and 20 ppm of ferrous sulfate, and 24 hours after dipping, the film sample was evaluated for the lapsing change from the appearance and weight change. When the film exhibited a good appearance and a weight retention of 95% or more, it was evaluated "good", whereas when any one of the appearance and the weight retention was insufficient, the film was evaluated "poor".

Temperature Dependence of Dynamic Viscoelasticity:

Using a dynamic viscoelasticity measurement device of tensile mode (frequency: 11 Hz), the film sample was measured for the tan δ peak temperature, which was then defined as a main dispersion temperature based on the glass transition.

SYNTHESIS EXAMPLE
Synthesis of Polymer of Monomer (A3)

67.3 g (0.20 moles) of 2,2-bis(4-hydroxyphenyl)-1,1,1,3,3,3-hexafluoropropane (bisphenol AF), 60.3 g (0.24 moles) of 4,4'-dichlorobenzophenone (4,4'-DCBP), 71.9 g (0.52 moles) of potassium carbonate, 300 ml of N,N-dimethylacetamide (DMAc), and 150 ml of toluene were introduced into a one-liter three-necked flask equipped with an agitator, a thermometer, a condenser, a Dean-Stark tube, and a three-way cock for nitrogen introduction, and the resulting mixture was reacted with stirring under heating at 130° C. in an oil bath under a nitrogen atmosphere. The reaction was proceeded while subjecting water as formed to azeotropic distillation with toluene and removing the azeotrope from the reaction system through the Dean-Stark tube. The formation of water was not substantially confirmed about 3 hours after the reaction. The reaction temperature was then gradually elevated from 130° C. to 150° C. Most of the toluene was removed while elevating the temperature to 150° C., and the reaction was continued at 150° C. for 10 hours. 10.0 g (0.040 moles) of 4,4'-DCBP was added to the reaction mixture, and the mixture was further reacted for 5 hours. After allowing the reaction mixture to stand for cooling, a precipitate of inorganic compounds formed as by-products was removed by filtration, and the filtrate was added into 4 liters of methanol. The precipitated product was filtered out, recovered, and then dried, followed by dissolving in 300 ml of tetrahydrofuran. The product was again precipitated in 4 liters of methanol to obtain 95.0 g (yield: 86.3%) of the desired compound.

The thus obtained polymer (condensate having a chlorobenzoyl group in the both terminal ends thereof [4,4'-dichlorobenzophenone 2,2-bis(4-hydroxyphenyl)-1,1,1,3,3,3-hexafluoropropane]) had a number average molecular weight of 12,200 and a weight average molecular weight of 26,800 as reduced into polystyrene by GPC (solvent: THF). Further, the obtained polymer was soluble in THF, NMP, DMAc, and sulfolane and had a Tg of 110° C. and a thermal decomposition temperature of 498° C.

It is assumed that the obtained polymer has a structure represented by the following formula:

thermometer, and the flask was purged with dry nitrogen. The reaction mixture was cooled to 10 to 15° C. while stirring, and 210 g (1.00 mole) of 2,5-dichlorobenzoic acid chloride was gradually added dropwise thereto from the dropping funnel. After completion of the dropwise addition, the reaction mixture was stirred for 3 hours while returning to room temperature.

The reaction mixture was poured into 3 liters of ice water containing 300 ml of concentrated hydrochloric acid, and the mixture was stirred. The solid was filtered out, washed with water, and then dissolved in 1.8 liters of ethyl acetate. The solution was successively washed with a 5% sodium hydrogencarbonate aqueous solution and saturated salt water, and then dried over magnesium sulfate. After filtration, the solvent and the excessive diphenyl ether were distilled off in vacuo. 650 ml of methanol for dissolution was added to the liquid residue, and water for crystallization was then added thereto. The crystal was recrystallized from ethyl acetate/n-hexane to obtain 265 g (yield: 77%) of the desired product having a melting point of 99 to 100° C.

(2) Synthesis of 2,5-dichloro-4'-[4-(4-fluorobenzoyl)phenoxy]benzophenone:

172 g (500 mmoles) of 2,5-dichloro-4'-phenoxybenzophenone and 86.7 g (650 mmoles) of aluminum chloride were introduced into a one-liter three-necked flask equipped with a dropping funnel, a nitrogen introduction tube, an agitating blade, and a thermometer, and the flask was purged with dry nitrogen. After adding 320 ml of dichloromethane, the flask was placed in an ice bath for cooling, and 87.2 g (550 mmoles) of 4-fluorobenzoic acid chloride was added dropwise to the reaction mixture with stirring. After completion of the dropwise addition, the ice bath was eliminated, and the reaction mixture was gradually returned to room temperature.

Three hours after the reaction, the reaction mixture was poured into 3 liters of ice water containing 400 ml of concentrated hydrochloric acid, and the mixture was stirred for a while. The product was extracted with 500 ml of dichloromethane, and the organic layer was successively washed with a 5% sodium hydrogencarbonate aqueous solution and salt water, followed by drying over magnesium sulfate. After filtration, the organic solvent was distilled off to obtain 221 g of a crude crystal of the desired product. The crude crystal was recrystallized from 500 ml of ethyl acetate to obtain 166 g (yield: 71%) of the desired product having a melting point of 109 to 111° C.

Figure 2:
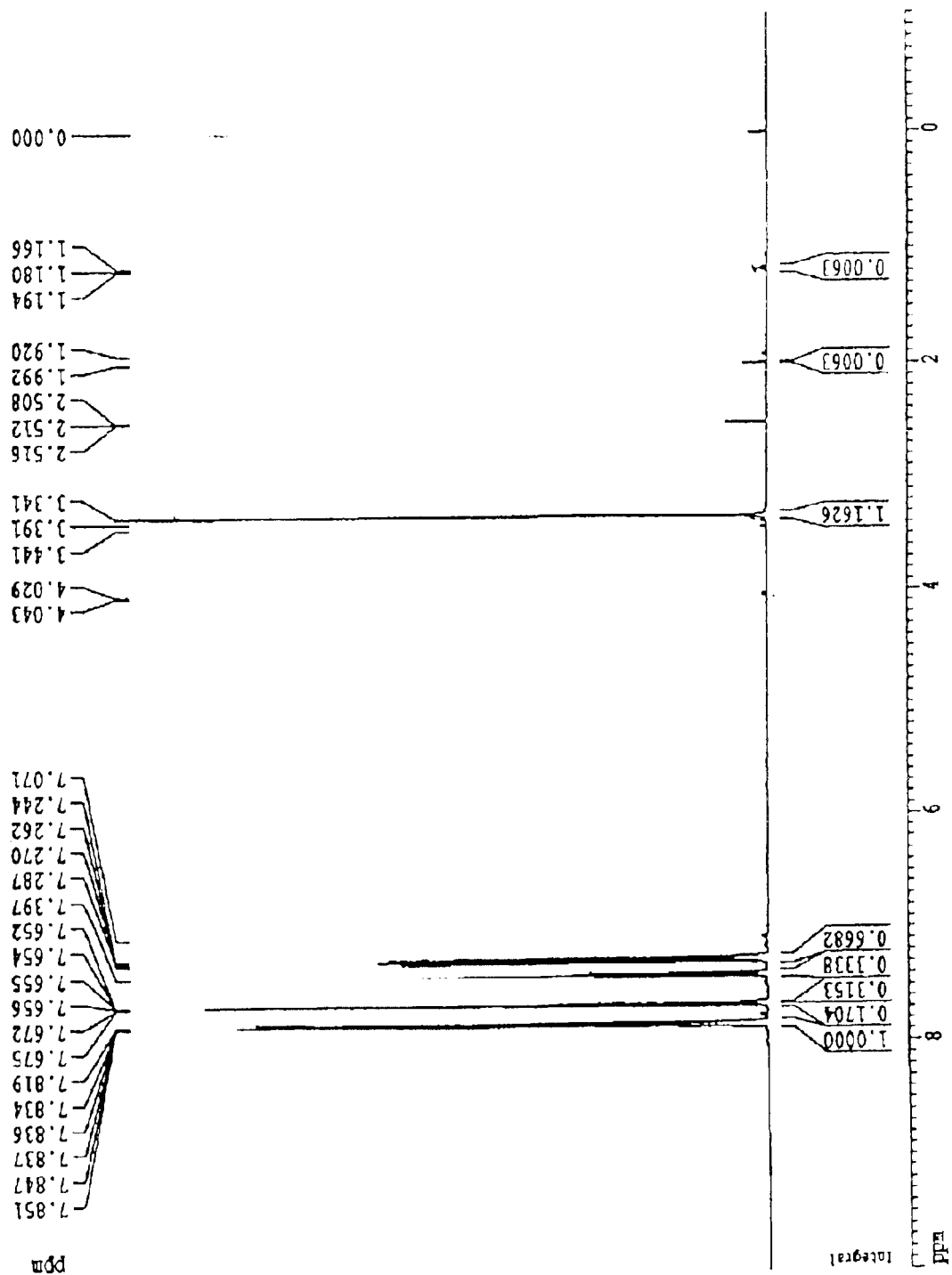
FIG. 2 is an NMR spectrum of 2,5-dichloro-4'-[4-(4-fluorobenzoyl)phenoxy]-benzophenone obtained in Example 1-(2).

The IR spectrum and NMR spectrum of the product are shown in FIG. 1 and FIG. 2, respectively.

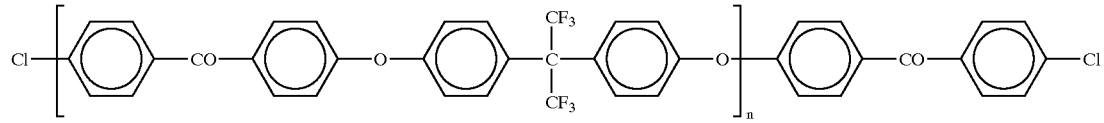

and the average value of n was determined to be 23.2 from the structure and the foregoing number average molecular weight.

EXAMPLE 1
Synthesis Examples of Monomers (1) Synthesis of 2,5-dichloro-4'-phenoxybenzophenone:

255 g (1.50 moles) of diphenyl ether and 173 g (1.30 moles) of aluminum chloride were introduced into a one-liter three-necked flask equipped with a dropping funnel, a nitrogen introduction tube, an agitating blade, and a (3) Synthesis of 2,5-dichloro-4'-[4-{4-(4-phenoxy)phenoxy}benzoyl]phenoxybenzo-phenone:

38.0 g (204 mmoles) of 4-phenoxyphenol, 36.7 g (265 mmoles) of potassium carbonate, 150 ml of toluene, and 300 ml of N,N-dimethylacetamide were introduced into a one-liter three-necked flask equipped with a Dean-Stark tube, a condenser, a nitrogen introduction tube, a thermometer, and an agitating blade. The content was refluxed with stirring upon heating at 130° C., and water formed was removed through the Dean-Stark tube. When the formation of water stopped, the toluene was distilled off from the reaction system while gradually elevating the temperature. After removing most of the toluene, 93.1 g (200 mmoles) of 2,5-dichloro-4'-[4-(4-fluorobenzoyl)phenoxy]benzophenone was added to the residue, and the mixture was allowed to react at 130° C. for 15 hours.

Figure 3:
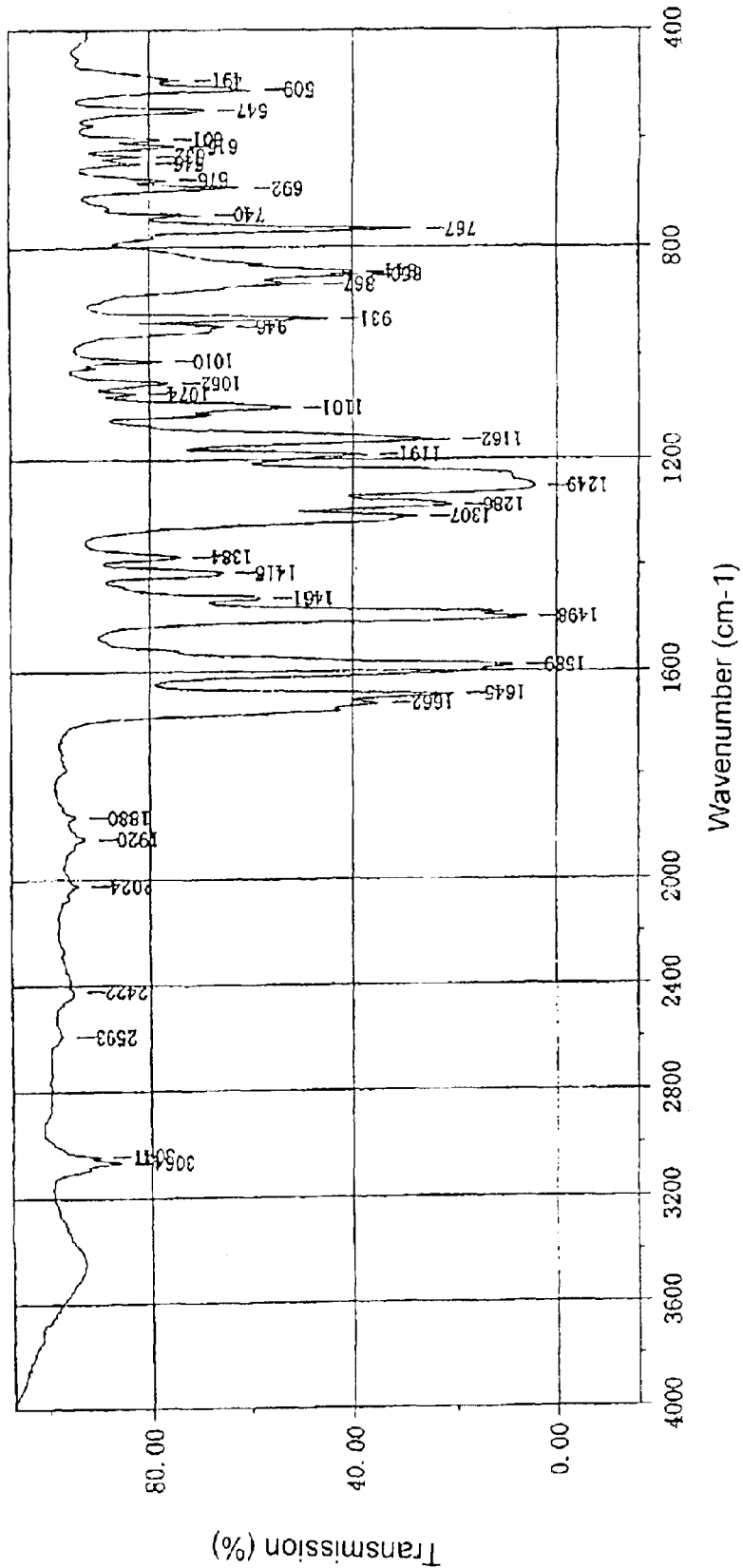
FIG. 3 is an IR spectrum of 2,5-dichloro-4'-[4-{4-(4-phenoxy)phenoxy}-benzoyl]phenoxybenzophenone obtained in Example 1-(3).

The reaction mixture was poured into 2.5 liters of water to form a precipitate. The precipitate was recovered by filtration, washed with 2.5 liters of methanol, and then dried in vacuo to obtain 140 g of a crude product. The crude product was dissolved in 1 liters of tetrahydrofuran, and the solution was again precipitated in 4 liters of methanol to obtain 94.5 g (yield: 75%) of the desired product having a melting point of 143 to 144° C. The IR spectrum of the product is shown in FIG. 3. In the IR spectrum, there are found the C—O—C absorption at 1,249 cm$^{-1}$ and the C=O absorption at 1,645 cm$^{-1}$. The product was soluble in N-methylpyrrolidone, dimethyl sulfoxide, and tetrahydrofuran and insoluble in methanol and water.

Figure 4:
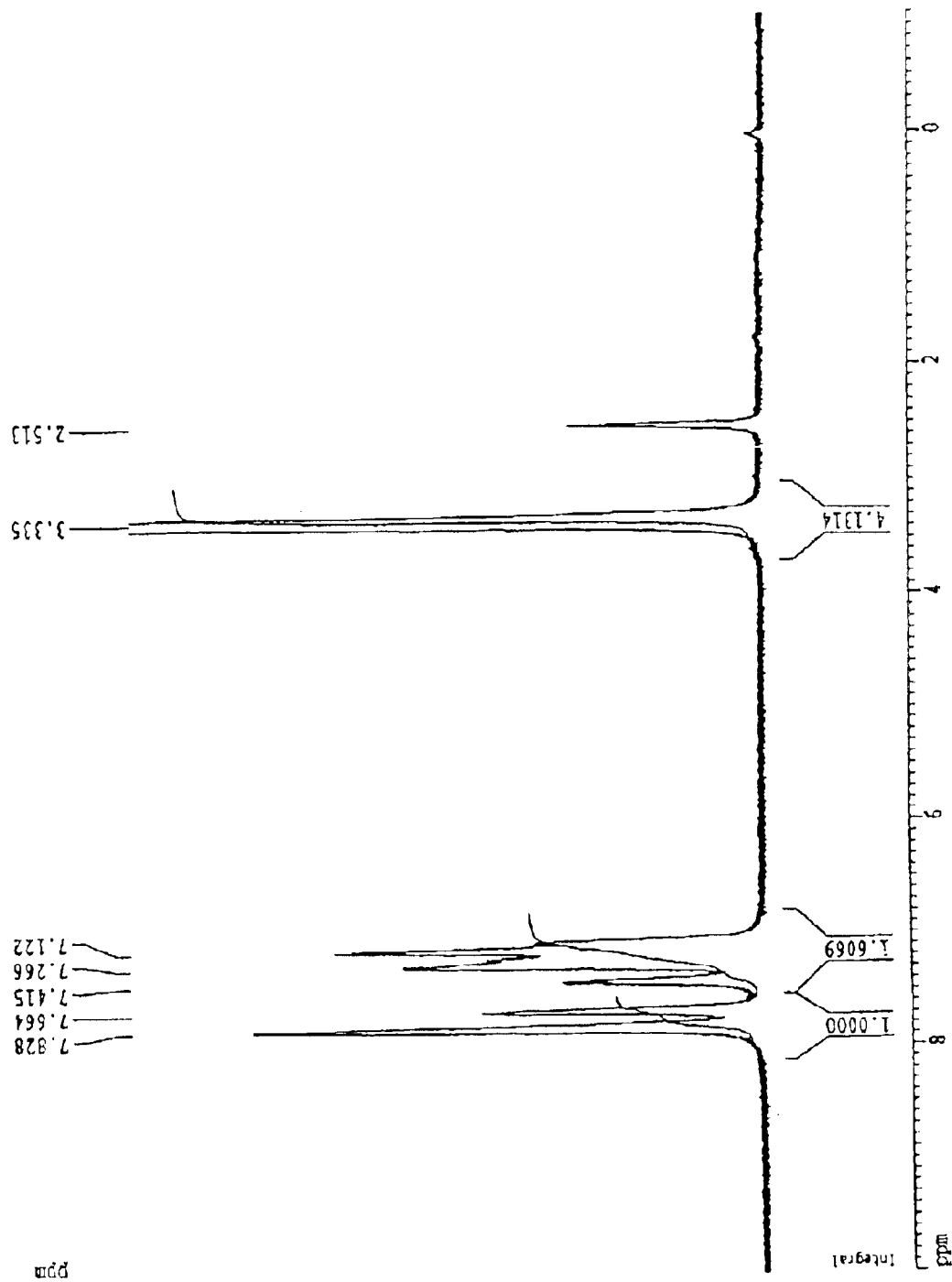
FIG. 4 is an NMR spectrum of 2,5-dichloro-4'-[4-{4-(4-phenoxy)phenoxy}-benzoyl]phenoxybenzophenone obtained in Example 1-(3).

The NMR spectrum of the product is shown in FIG. 4.

EXAMPLE 2

(1) Preparation of Base Polymer:

12.3 g (19.5 mmoles) of 2,5-dichloro-4'-[4-{4-(4-phenoxy)phenoxy}-benzoyl]phenoxybenzophene, 6.83 g (0.560 mmole chlorobenzoyl group in the both terminal ends thereof [4,4'-dichlorobenzophenone 2,2-bis(4-hydroxyphenyl)-1,1,1,3,3,3-hexafluoropropane]) (number average molecular weight: 12,200) as obtained in the foregoing Synthesis Example, 0.589 g (0.900 mmoles) of bis(triphenylphosphine)nickel dichloride, 0.507 g (3.38 mmoles) of sodium iodide, 2.73 g (10.4 mmoles) of triphenylphosphine, and 4.08 g (62.4 mmoles) of zinc were introduced into a 500 ml three-necked flask equipped with an agitating blade, a thermometer, and a condenser, and the mixture was dried in vacuo. The flask was purged with dry nitrogen, 54.6 ml of N-methylpyrrolidone was added thereto, and the mixture was polymerized with stirring in an oil bath at 80° C.

Figure 5:
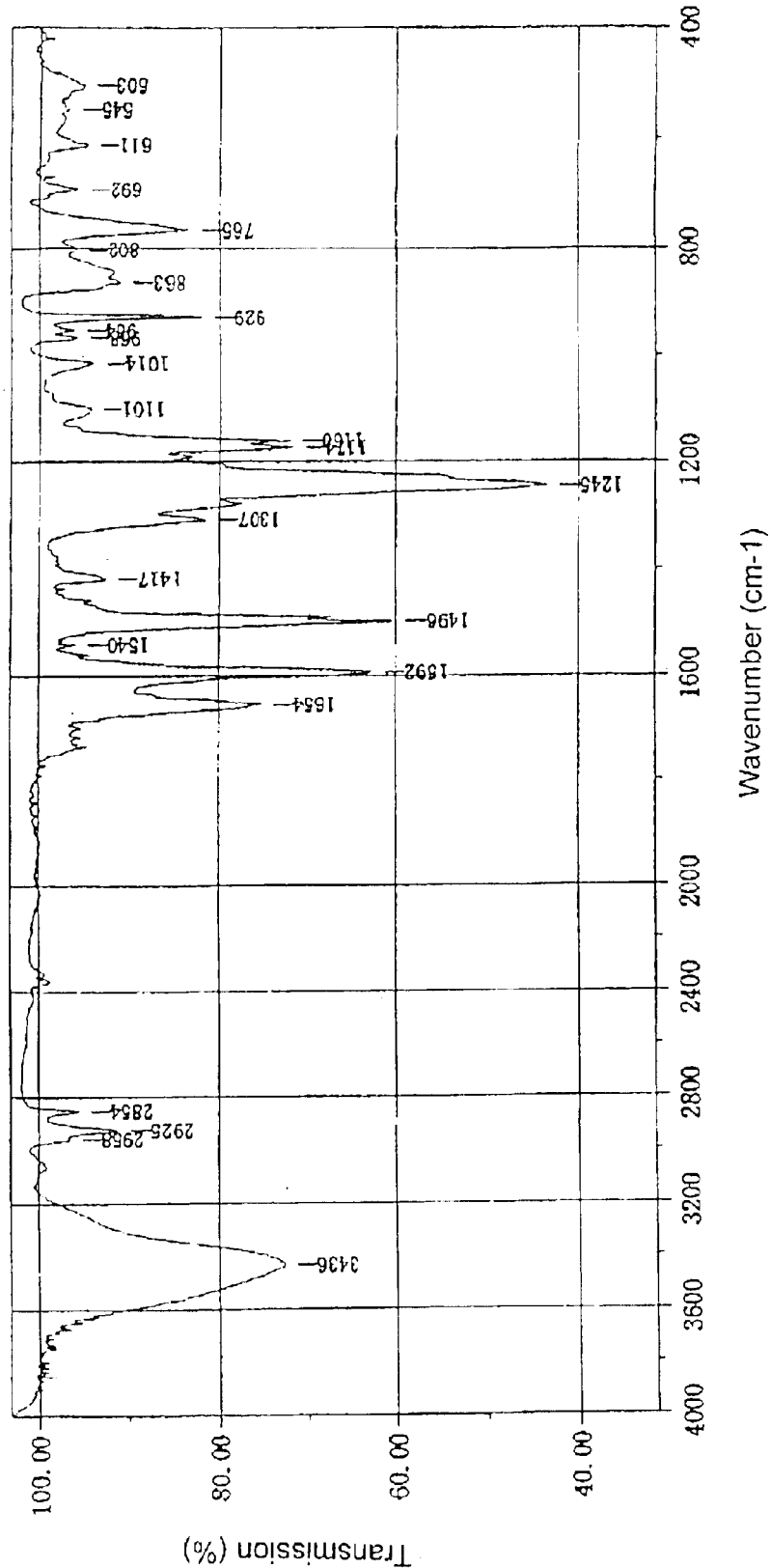
FIG. 5 is an IR spectrum of the base polymer obtained in Example 2-(1).

Three hours after the polymerization, the polymerization solution was added to 3 liters of methanol containing 10 volume % concentrated hydrochloric acid to precipitate the polymer. The polymer was taken out, dried, and then dissolved in 300 ml of tetrahydrofuran. The insoluble matter was filtered out. The resulting solution was again precipitated in 3 liters of methanol to obtain 16.2 g (yield: 91.5%) of the desired polymer. This polymer had a number average molecular weight of 41,800 and a weight average molecular weight of 115,000 as reduced into polystyrene by GPC. The IR spectrum of the resulting polymer is shown in FIG. 5. In the IR spectrum, there are found the C—O—C absorption at 1,245 cm$^{-1}$ and the C=O absorption at 1,654 cm$^{-1}$. The polymer was soluble in N-methylpyrrolidone and tetrahydrofuran and insoluble in acetone, methanol, and water.

Figure 6:
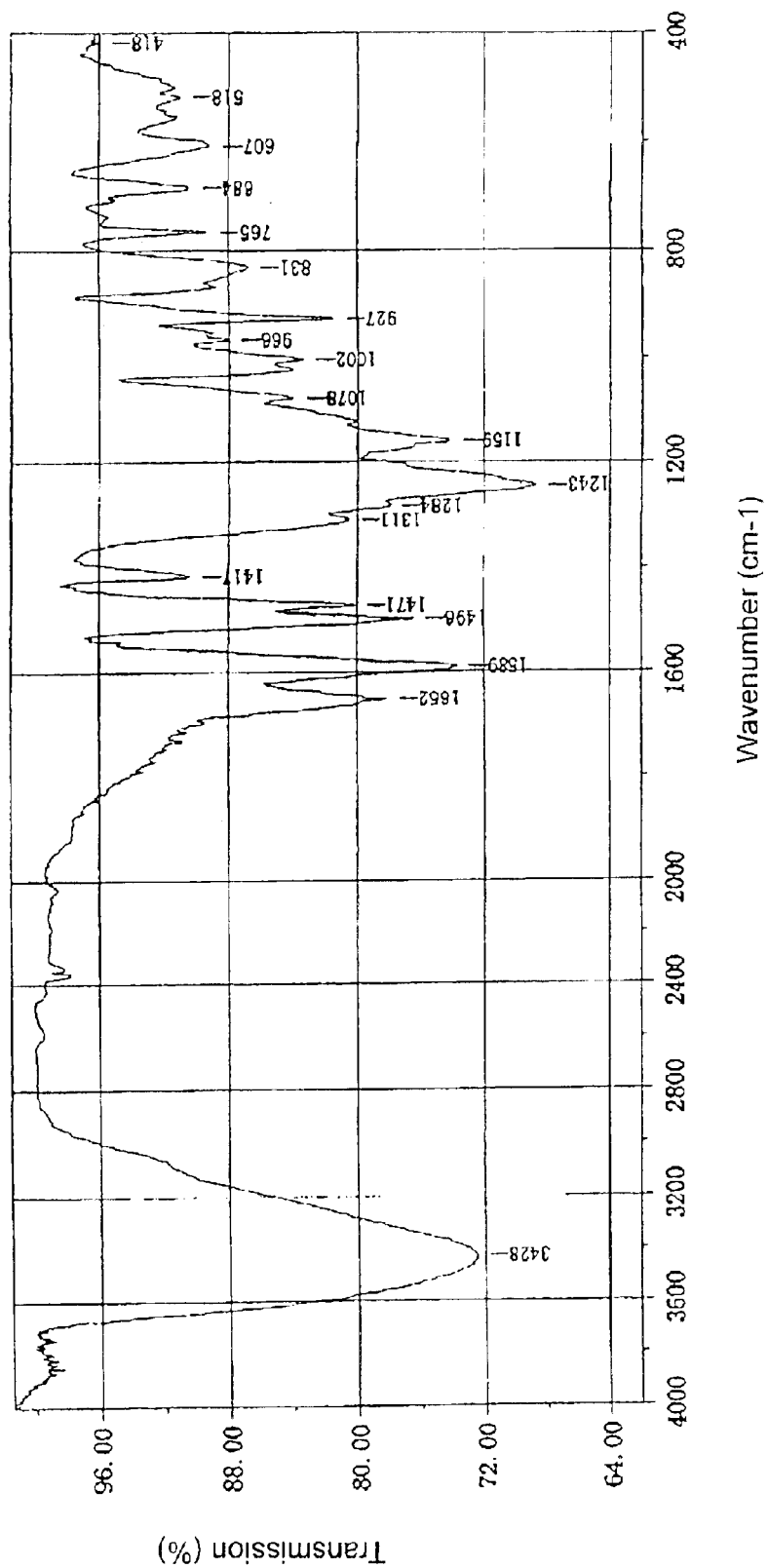
FIG. 6 is an IR spectrum of the sulfonated polymer obtained in Example 2-(2).

(2) Preparation of Sulfonated Polymer:

15 g of the polymer obtained in (1) above was added to 150 ml of concentrated sulfuric acid, and the mixture was stirred at room temperature for 24 hours to prepare a sulfonated polymer. The reaction mixture was added to 5 liters of distilled water to precipitate the sulfonated product. The precipitate was ground by a mixer and repeatedly washed with 5 liters of distilled water until the washings became neutral. The product was dried by hot air to obtain 16 g of the sulfonated polymer. This polymer had an ion exchange capacity of 1.8 mg-eq./g. The IR spectrum of the sulfonated product is shown in FIG. 6. In the IR spectrum, there are found the S=O absorption at 1,159 cm$^{-1}$, the C—O—C absorption at 1,243 cm$^{-1}$, and the C=O absorption at 1,652 cm$^{-1}$. The polymer was soluble in N-methylpyrrolidone and tetrahydrofuran and insoluble in acetone, methanol, and water.

(3) Preparation of Proton-Conductive Membrane:

The sulfonated polymer as obtained in (2) above was dissolved in a mixed solvent of NMP and methanol (50/50 in a volume ratio) to prepare a 15 weight % polymer solution, from which was then formed a film by using a doctor blade. The film was dried at 100° C. for 30 minutes and then at 150° C. for one hour. The resulting film was dipped in water for 4 hours to extract the solvent contained in the film. After the extraction, water on the surface was swept away, and the film was air-dried in a constant temperature and humidity chamber at 25° C. and at 50% RH for 24 hours to prepare a film for evaluation. The resulting film was measured for proton conductivity, kinetic properties: tensile strength properties (elastic modulus, yield strength, tensile strength, and elongation), hot water resistance, resistance to Fenton's reagent, and thermal properties (temperature dependence of dynamic viscoelasticity and thermal decomposition temperature). The results are shown in Table 1.

EXAMPLE 3

(1) Base Polymer:

The polymerization was carried out in the same manner as in Example 2-(1), except for changing the charge amounts of the 2,5-dichloro-4'-[4-{4-(4-phenoxy)phenoxy}benzoyl]phenoxybenzophenone, the condensate having a chlorobenzoyl group in the both terminal ends thereof [4,4'-dichlorobenzophenone 2,2-bis(4-hydroxyphenyl)-1,1,1,3,3,3-hexafluoropropane]) (number average molecular weight: 12,200), and the N-methylpyrrolidone to 12.2 g (19.2 mmoles), 9.27 g (0.760 mmoles) and 61.2 ml, respectively. There was thus obtained 18.1 g (yield: 90.5%) of the desired polymer. This polymer had a number average molecular weight of 40,900 and a weight average molecular weight of 114,000 as reduced into polystyrene by GPC.

(2) Sulfonated Polymer:

The sulfonation was carried out in the same manner as in Example 2-(2). The obtained polymer had an ion exchange capacity of 1.6 mg-eq./g.

(3) Preparation of Proton-Conductive Membrane:

A film was prepared and evaluated in the same manner as in Example 2-(3).

The results are shown in the Table below.

TABLE

| Ex-ample No. | Proton conduct-ivity (S/cm) | Tensile strength properties | | | |
|---|---|---|---|---|---|
| | | Elastic modulus (Gpa) | Yield strength (MPa) | Tensile strength (MPa) | Elongation (%) |
| 2 | 0.14 | 3.1 | 72 | 72 | 65 |
| 3 | 0.10 | 3.2 | 72 | 76 | 56 |
| | | Thermal | | | |

TABLE-continued

| Example No. | Hot water resistance | Resistance to Fenton's reagent | properties Dynamic viscoelasticity |
|---|---|---|---|
| 2 | Good | Good | >150° C. |
| 3 | Good | Good | >150° C. |

The halogenated aromatic compound according to the invention is useful for incorporating a sulfonic acid group having a high activity of proton conductivity during the sulfonation of (co)polymer, and the resulting sulfonic acid group-containing (co)polymer is useful as a proton-conductive membrane material.

The proton-conductive membrane comprising the sulfonated polyarylene (co)polymer according to the invention can realize a proton conductivity equal to that conventionally sulfonated (co)polymers even at a low sulfonic acid group equivalent. Consequently, it is possible to inhibit a reduction of physical properties (such as hot water resistance, toughness, and oxidation resistance) caused by the usual sulfonation.

Consequently, the proton-conductive membrane according to the invention can be used as a proton-conductive membrane for primary battery electrolyte, secondary batter electrolyte, fuel cell polymer solid electrolyte, display element, various sensors, signal medium, solid capacitor, ion exchange membrane, etc. and hence, is greatly meaningful from the industrial viewpoint.

It should further be apparent to those skilled in the art that various changes in form and detail of the invention as shown and described above may be made. It is intended that such changes be included within the spirit and scope of the claims appended hereto.

This application is based on Japanese Patent Application No. 2002-13450, filed Jan. 22, 2002, the disclosure of which is incorporated herein by reference in its entirety.

What is claimed is:

1. A halogenated aromatic compound represented by the following general formula (1bm):

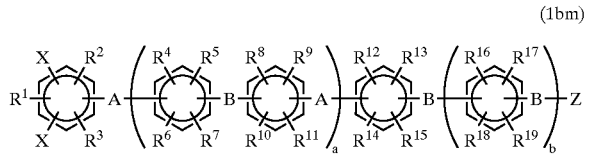

(1bm)

wherein As' independently represent an electron-withdrawing group; Bs' independently represent an electron-donating atom or divalent group; Xs' independently represent a chlorine atom, an iodine atom, or a bromine atom; Z represents an aryl group; $R^1$ to $R^{19}$ may be the same or different and each represents a hydrogen atom, a fluorine atom, an alkyl group, or a fluoroalkyl group; and a and b each represents an integer of 1 to 20.

2. The halogenated aromatic compound according to claim 1, wherein in the general formula (1bm), the electron-withdrawing group A is >C=O, and the electron-donating atom B is —O—.

3. The halogenated aromatic compound according to claim 1, which is 2,5-dichloro-4'-[4-{4-(4-phenoxy)phenoxy}benzoyl]phenoxybenzophenone.

4. A polyarylene (co)polymer having a repeating unit represented by the following general formula (1b):

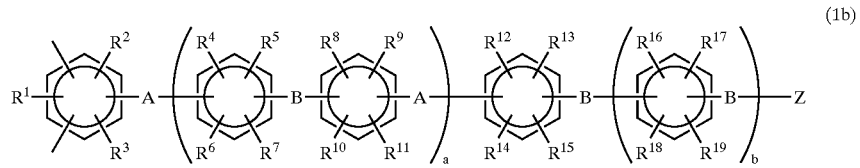

(1b)

wherein As' independently represent an electron-withdrawing group; Bs' independently represent an electron-donating atom or divalent group; Xs' independently represent a chlorine atom, an iodine atom, or a bromine atom; Z represents an aryl group; $R^1$ to $R^{19}$ may be the same or different and each represents a hydrogen atom, a fluorine atom, an alkyl group, or a fluoroalkyl group; and a and b each represents an integer of 1 or more.

5. The polyarylene (co)polymer according to claim 4, wherein in the general formula (1b), the electron-withdrawing group A is >C=O, and the electron-donating atom B is —O—.

6. The polyarylene (co)polymer according to claim 4, which is a polyarylene copolymer having a repeating unit represented by the general formula (1b) and a repeating unit comprising other divalent aromatic group.

7. The polyarylene (co)polymer according to claim 6, wherein the repeating unit comprising other divalent aromatic group is a unit presented by the following general formula (1a):

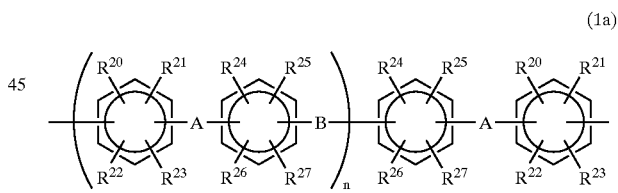

(1a)

wherein As' independently represent an electron-withdrawing group; Bs' independently represent an electron-donating atom or divalent group; $R^{20}$ to $R^{27}$ may be the same or different and each represents a hydrogen atom, a fluorine atom, an alkyl group, or a fluoroalkyl group; and n represents 0 or an integer of 1 or more.

8. The polyarylene (co)polymer according to claim 4, further containing a sulfonic acid group in the molecule thereof.

9. The polyarylene (co)polymer according to claim 8, containing from 0.5 to 3.0 meq./g of the sulfonic acid group.

10. A proton-conductive membrane comprising the sulfonic acid group-containing polyarylene (co)polymer according to claim 8.

* * * * *